US008142369B2

(12) United States Patent
Sanders et al.

(10) Patent No.: US 8,142,369 B2
(45) Date of Patent: Mar. 27, 2012

(54) MEASUREMENT AND USE OF IN-SOCKET RESIDUAL LIMB VOLUME CHANGE DATA FOR PROSTHETIC FITTING

(75) Inventors: Joan E. Sanders, Sammamish, WA (US); Timothy R. Myers, Seattle, WA (US); Daniel S. Harrison, Kirkland, WA (US); Katheryn J. Allyn, Seattle, WA (US); Ellen L. Lee, Corvallis, OR (US); Daniel C. Abrahamson, Seattle, WA (US); Kirk Beach, Seattle, WA (US); Santosh Zachariah, Seattle, WA (US)

(73) Assignee: University of Washington, Seattle, WA (US)

( * ) Notice: Subject to any disclaimer, the term of this patent is extended or adjusted under 35 U.S.C. 154(b) by 376 days.

(21) Appl. No.: 12/509,934

(22) Filed: Jul. 27, 2009

(65) Prior Publication Data

US 2010/0036455 A1  Feb. 11, 2010

Related U.S. Application Data

(60) Provisional application No. 61/084,193, filed on Jul. 28, 2008.

(51) Int. Cl.
*A61B 5/1477* (2006.01)
(52) U.S. Cl. ......... 600/587; 607/148; 600/382; 600/456
(58) Field of Classification Search .................. 607/148; 600/382, 456, 587
See application file for complete search history.

(56) References Cited

U.S. PATENT DOCUMENTS

| | | | |
|---|---|---|---|
| 4,875,488 A * | 10/1989 | Shimazu et al. | 600/507 |
| 5,280,429 A | 1/1994 | Withers | 364/413.15 |
| 6,125,297 A | 9/2000 | Siconolfi | 600/547 |
| 6,151,523 A | 11/2000 | Rosell Ferrer et al. | 600/547 |
| 6,690,181 B1 | 2/2004 | Dowdeswell et al. | 324/691 |
| 6,927,858 B2 | 8/2005 | Boone et al. | 356/437 |
| 6,980,852 B2 * | 12/2005 | Jersey-Willuhn et al. | 600/547 |
| 7,150,762 B2 | 12/2006 | Caspers | 623/27 |
| 7,310,999 B2 | 12/2007 | Miller | 73/149 |

(Continued)

OTHER PUBLICATIONS

Chaudhari et al., "Hyperspectral and multispectral bioluminescence optical tomography for small animal imaging." *Physics in Medicine and Biology* vol. 50, No. 23: 5421-5441, Dec. 7, 2005.

(Continued)

*Primary Examiner* — Carl H Layno
*Assistant Examiner* — Natasha Patel
(74) *Attorney, Agent, or Firm* — Kilpatrick Townsend & Stockton LLP

(57) ABSTRACT

Changes in the volume of residual limbs on which prosthetic sockets are worn can be measured based on bioimpedance measurements along one or more segments of the limb. A current at an appropriate frequency (e.g., in the range from 1 kHz to 1 MHz) is injected at two current electrodes that contact the skin of the residual limb. The voltage at the voltage electrodes disposed between the current electrodes is measured and using an appropriate model, the change in the segmented volume of the limb can be determined during periods of different activity and at different times during the day. This information can be used for assessing the fit of the socket and can also provide a feedback signal for automatically controlling volume management devices, to ensure a more comfortable fit when the volume of the limb is changing.

40 Claims, 13 Drawing Sheets

U.S. PATENT DOCUMENTS

| | | | |
|---|---|---|---|
| 7,794,505 B2 | 9/2010 | Clausen et al. | 623/50 |
| 2007/0191965 A1 | 8/2007 | Colvin et al. | 623/34 |
| 2008/0200994 A1 | 8/2008 | Colgate et al. | 623/24 |

OTHER PUBLICATIONS

Meijer et al., "Method for the measurement of susceptibility to decubitus ulcer formation." *Medical & Biological Engineering & Computing* vol. 27(5): 502-506, 1989.

Meijer et al. "Susceptibility to decubitus ulcer formation." *Archives of Physical Medicine and Rehabilitation* vol. 75(3): 318-323, 1994.

Mein et al., "Skin temperature response to a pressure load: studies in subjects before and during spinal anesthesia." *Archives of Physical Medicine and Rehabilitation* vol. 76(3): 243-245, 1995.

Sanders, J.E., "Thermal response of skin to cyclic pressure and pressure with shear: a technical note." *Journal of Rehabilitation Research and Development* vol. 37, No. 5: 511-515, 2000.

van Marum et al., "Impaired blood flow response following pressure load in diabetic patients with cardiac autonomic neuropathy." *Archives of Physical Medicine and Rehabilitation* vol. 78(9): 1003-1006, 1997.

van Marum et al., "Relationship between internal risk factors for development of decubitus ulcers and the blood flow response following pressure load." *Angiology* vol. 52(6): 409-416, 2001.

van Marum et al., "The relationship between pressure ulcers and skin blood flow response after a local cold provocation." *Archives of Physical Medicine and Rehabilitation* vol. 83(1): 40-43, 2002.

Boone et al., "Automated fabrication of mobility aids: Review of the AFMA process and VA/Seattle ShapeMaker software design." *Journal of Rehabilitation Research and Development* vol. 31, No. 1: 42-49, 1994.

Boone et al., "Automated Fabrication of Mobility Aids: Clinical Demonstration of the UCL Computer Aided Socket Design System," *Journal of Prosthetics and Orthotics* vol. 1, No. 3: 187-190, 1989.

Chan et al., "Dynamic Rectification: A Statistically Based Evolving Socket Rectification Mechanism." *7th World Congress of the International Society for Prosthetics and Orthotics* Chicago, IL: 27, Jun. 28-Jul. 3, 1992.

Chan et al., "Surface Curvature Analysis for Enhanced Computer-Aided-Design of Prosthetic Sockets." *IEEE* 1292-1293, 1993.

Commean et al., "Design of a 3-D surface scanner for lower limb prosthetics: A technical note." *Journal of Rehabilitation Research and Development* vol. 33, No. 2: 267-278, 1996.

Convery et al., "Measurement of the consistency of patellar-tendon-bearing cast rectification." *Prosthetics and Orthotics International* vol. 27, No. 3: 207-213, 2003.

Dean et al., "A Software Package for Design and Manufacture of Prosthetic Sockets for Transtibial Amputees," *IEEE Transactions on Biomedical Engineering* vol. 32, No. 4: 257-262, 1985.

Hastings et al., "Frequency Content of Prosthetic and Orthotic Shapes: A Requirement for CAD/CAM Digitizer Performance." *Journal of Prosthetics and Orthotics* vol. 10, No. 1: 2-6, 1998.

He et al., "Test of a vertical scan mode in 3-D imaging of residual limbs using ultrasound." *Journal of Rehabilitation Research and Development* vol. 36, No. 2: 14pp., 1999.

Houston et al., "Automated fabrication of mobility aids (AFMA): Below-knee CASD/CAM testing and evaluation program results." *Journal of Rehabilitation Research and Development* vol. 29, No. 4: 78-124, 1992.

Houston et al., "The VA-Cyberware lower limb prosthetics-orthotics optical laser digitizer." *Journal of Rehabilitation Research and Development* vol. 32. No. 1: 55-73, 1995.

Johansson et al., "Accuracy and precision of volumetric determinations using two commercial CAD systems for prosthetics: A technical note." *Journal of Rehabilitation Research and Development* vol. 35, No. 1: 27-33, 1998.

Krouskop et al., "Measuring the shape and volume of an above-knee stump." *Prosthetics and Orthotics International* vol. 12, No. 3: 136-142, 1988.

Kulczycka et al., "Qualitative and quantitative comparisons of B-spline offset surface approximation method." *Computer-Aided Design* vol. 34: 19-26, 2002.

Lemaire, E., "A CAD analysis programme for prosthetics and orthotics." *Prosthetics and Orthotics International* vol. 18, No. 2: 112-117, 1994.

Lemaire et al., "A Quantitative Method for Comparing and Evaluating Manual Prosthetic Socket Modifications." *IEEE Transactions on Rehabilitation Engineering* vol. 4, No. 4: 303-309, 1996.

Lemaire et al., "Validation of a quantitative method for defining CAD/CAM socket modifications." *Prosthetics and Orthotics International* vol. 23, No. 1: 30-44, 1999.

Lilja et al., "Proper Time for Definitive Transtibial Prosthetic Fitting." *Journal of Prosthetics and Orthotics* vol. 9, No. 2: 90-95, 1997.

Lilja et al., "Volumetric determinations with CAD/CAM in prosthetics and orthotics: Error of measurement." *Journal of Rehabilitation Research and Development* vol. 32, No. 2: 141-148, 1995.

McGarry et al., "Evaluation of a contemporary CAD/CAM system." *Prosthetics and Orthotics International* vol. 29, No. 3: 221-229, 2005.

McGarry et al., "Evaluation of the effect of shape on a contemporary CAD system." *Prosthetics and Orthotics International* vol. 32, No. 2: 145-154, 2008.

Sanders et al., "A digitizer with exceptional accuracy for use in prosthetic research: A technical note", *Journal of Rehabilitation Research and Development*, vol. 40, No. 2; Mar./Apr. 2003; pp. 191-196.

Sanders et al., "CAD/CAM transtibial prosthetic sockets from central fabrication facilities: How accurate are they?", *Journal of Rehabilitation Research and Development*, vol. 44, No. 3; 2007; pp. 395-406.

Sidles et al., "A quantitative comparison of amputee stump and socket shapes." *Proceedings of the 35th Annual Meeting—Orthopaedic Research Society* Las Vegas, NV: Feb. 1989.

Sidles et al., "Mathematical techniques for comparing residual limb and sockate shapes." *Proceedings of the ISPO Sixth World Congress* Kobe, Japan: Nov. 1989.

Sidles et al., "Rectification Maps: A New Method for Describing Residual Limb and Socket Shapes." *Journal of Prosthetics and Orthotics* vol. 1, No. 3: 149-153, 1989.

Sidles et al., "Rectification Maps: A New Method for Describing Stump and Socket Shapes." In: Davies et al., eds. *Report of the ISPO Workshop on CAD/CAM in Prosthetics and Orthotics* Seattle, WA; Copenhagen, Denmark; International Society of Prosthotists and Orthotists: 15-18, 1988, 1990.

Smith et al., "Validation of spiral CT and optical surface scanning for lower limb stump volumetry." *Prosthetics and Orthotics International* vol. 19, No. 2: 97-107, 1995.

Torres-Moreno et al., "A reference shape library for computer aided socket design in above-knee prostheses." *Prosthetics and Orthotics International* vol. 13, No. 3: 130-139, 1989.

Travis et al., "Computer-aided socket design for trans-femoral amputees." *Prosthetics and Orthotics International* vol. 17, No. 3: 172-179, 1993.

Vannier et al., "Three-Dimensional Lower-Extremity Residua Measurement Systems Error Analysis." *Journal of Prosthetics and Orthotics* vol. 9, No. 2: 67-76, 1997.

Walsh et al., "A Computerized System to Manufacture Prostheses for Amputees in Developing Countries." *Journal of Prosthetics and Orthotics* vol. 1, No. 3: 165-181, 1989.

Zachariah et al., "A Method for Aligning Trans-Tibial Residual Limb Shapes So as to Identify Regions of Shape Change", IEEE Transactions on Neural Systems and Rehabilitation Engineering, vol. 13, No. 4; Dec. 2005; pp. 551-557.

Cotton et al., "A Novel Thick-Film Piezoelectric Slip Sensor for a Prosthetic Hand." *IEEE Sensors Journal*, vol. 7, No. 5: 752-761, May 2007.

Armstrong et al., "Bioimpedance spectroscopy technique: Intra-, extracellular, and total body water." *Medicine & Science in Sports & Exercise* vol. 29(12): 1657-1663, 1997.

Cole et al., "Electrical analogues for tissues." *Experimental Neurology* vol. 24(3): 459-473, 1969.

De Lorenzo et al., "Predicting body cell mass with bioimpedance by using theoretical methods: a technological review." *Journal of Applied Physiology* vol. 82(5): 1542-1558, 1997.

Donadio et al., "Estimate of body water compartments and of body composition in maintenance hemodialysis patients: Comparison of single and multifrequency bioimpedance analysis." *Journal of Renal Nutrition* vol. 15, No. 3: 332-344, 2005.

Fenech et al., "Extracellular and intracellular volume variations during postural change measured by segmental and wrist-ankle bioimpedance spectroscopy." *IEEE Transactions on Biomedical Engineering* vol. 51, No. 1: 166-175, 2004.

Fuller et al., "Predicting composition of leg sections with anthropometry and bioelectrical impedance analysis, using magnetic resonance imaging as reference." *Clinical Science* London; vol. 96(6): 647-657, 1999.

Gilbert et al., "Effect of frequency, circuit analysis and instrument on extracellular and total body resistance." *Medicine & Science in Sports & Exercise* 672 Suppl: S118, 1995.

Hanai T., "Electrical Properties of Emulsions." In: Sherman P, editor. *Emulsion Science* London, England, Academic Press: 354-477, 1968.

Hoffer et al., "Correlation of whole-body impedance with total body water volume." *Journal of Applied Physiology* vol. 27, No. 4: 531-534, 1969.

Matthie et al., "Analytic assessment of the various bioimpedance methods used to estimate body water." *Journal of Applied Physiology* vol. 84(5): 1801-1816, 1998.

Nyboer J., "Workable volume and flow concepts of biosegments by electrical impedance plethysmography." *T.I.T Journal of Life Sciences* vol. 2(1): 1-13, 1972; Reprinted in *Nutrition* vol. 7, No. 6: 396-408, 1991.

Organ et al., "Segmental bioelectrical impedance analysis: Theory and application of a new technique." *Journal of Applied Physiology* vol. 77(1): 98-112, 1994.

Salinari et al., "Bioimpedance analysis: A useful technique for assessing appendicular lean soft tissue mass and distribution." *Journal of Applied Physiology* vol. 94(4): 1552-1556, 2003.

Sanders et al., "Assessment of residual-limb volume change using bioimpedance." *Journal of Rehabilitation Research & Development* vol. 44, No. 4: 525-536. 2007.

Sanders et al., "Bioimpedance Analysis and Diurnal Volume Change: Assessment on Trans-Tibial Amputee Prosthesis Users." *Archives of Physical Medicine and Rehabilitation* pp. 1-22, submitted 2008.

Sanders et al., "Clinical utility of in-socket residual limb volume change measurement: Case study results." *Prosthetics and Orthotics International* pp. 1-29, submitted 2009.

Segal et al., "Estimation of extracellular and total body water by multiple-frequency bioelectrical-impedance measurement." *The American Journal of Clinical Nutrition* vol. 54(1): 26-29, 1991.

Siconolfi et al., "Assessing total body and extracellular water from bioelectrical response spectroscopy." *Journal of Applied Physiology* vol. 82(2): 704-710, 1997.

Thomas et al., "A comparison of segmental and wrist-to-ankle methodologies of bioimpedance analysis." *Applied Radiation Isotopes* vol. 49, No. 5/6: 477-78, 1998.

Van Loan et al., "Use of bioimpedance spectroscopy to determine extracellular fluid, intracellular fluid, total body water, and fat-free mass." *Human Body Composition: in vivo Methods, Models, and Assessment* Edited by: Ellis, New York: 67-70, 1993.

Wotton et al., "Comparison of whole body and segmental bioimpedance methodologies for estimating total body water." *Annals New York Academy of Sciences* 904: 181-186, 2000.

Zachariah et al., "Shape and volume change in the transtibial residuum over the short term: Preliminary investigation of six subjects." *Journal of Rehabilitation Research & Development* vol. 41, No. 5: 683-694, 2004.

Zhu et al., "Dynamics of segmental extracellular volumes during changes in body position by bioimpedance analysis." *Journal of Applied Physiology* vol. 85(2): 497-504, 1998.

Zhu et al., "Methods and reproducibility of measurement of resistivity in the calf using regional bioimpedance analysis." *Blood Purification* vol. 21: 131-136, 2003.

Zhu et al., "Validation of changes in extracellular volume measured during hemodialysis using a segmental bioimpedance technique." *ASAIO Journal* vol. 44(5): M541-545, 1998.

\* cited by examiner

LIMB VOLUME CHANGE DURING STANDING

MEASUREMENT AND USE OF IN-SOCKET RESIDUAL LIMB VOLUME CHANGE DATA FOR PROSTHETIC FITTING

GOVERNMENT RIGHTS

This invention was made with U.S. government support under Grant No. R01-EB004329 awarded by the National Institutes of Health (NIH). The U.S. government has certain rights in the invention.

RELATED APPLICATIONS

This application is based on a prior copending provisional application Ser. No. 61/084,193, filed on Jul. 28, 2008, the benefit of the filing date of which is hereby claimed under 35 U.S.C. §119(e).

BACKGROUND

Residual limb volume fluctuation is an important challenge for amputee prosthesis users. When the volume of the residual limb changes, the prosthesis fits differently. If the residual limb reduces in volume, as usually occurs over the course of a day for example, the limb becomes loose in the prosthetic socket, and stresses can concentrate in soft tissues over bony prominences, causing pain. The risk of limb injury is also increased. If the residual limb increases in volume in the socket, interstitial fluid pressure increases, potentially occluding blood flow through the residual limb. Tissues are denied nutrients, and restricted venous return can cause a buildup of cell waste products and deterioration of limb tissues. Both of these conditions can result in soft tissue injury. Accordingly, residual limb volume fluctuation has been recognized as a major challenge that should be a priority in prosthetics research. Given that residual limb breakdown occurs in as much as 24% to 41% of the amputee population at a time and that limb volume fluctuation is considered a principal cause of pain and tissue breakdown, efforts to understand and control limb volume change are clearly of major significance.

Part of the difficulty for practitioners in helping patients to manage limb volume fluctuation is the lack of a quick and quantitative means for assessment. Current practices for assessing volume change are slow and highly subjective. A practitioner typically asks a patient about limb pain and sock ply variation throughout the day, since, for example, as a residual limb reduces in volume during the day, the patient may add socks to the limb to improve its fit in the socket. That information is coupled with an understanding of the patient's pathology and an inspection of the residual limb. Tests that include the patient adding or removing socks during the day are used over a trial period. The clinician then makes an educated guess about what (if anything) needs to be done to the socket to improve the fit. During these efforts, the patient's limb is at risk.

Quantitative assessment should substantially speed up the process of diagnosing and deciding treatment for limb volume fluctuation, from weeks to minutes and allow insight early on in fitting the socket to the limb. Further, quantitative measurement should not only help in understanding the expected diurnal fluctuation of residual limb volume, but should also provide insight into its source.

Ideally, the measurement of volume change of the residual limb should continue throughout the day, as the patient engages in normal activities, since the effect of such activities on the volume of the limb can be important in assessing whether and how to modify a socket to achieve a better fit. The data relating to volume change should thus be recorded for an extended period, while the patient is mobile. To enable such mobility, the hardware that detects changes in the volume of the residual limb must be relatively compact and not interfere with the fit of the prosthetic socket on the residual limb.

One approach for measuring the volume of a residual limb is to monitor the bioimpedance of the limb over time. Several bioimpedance measurement products are commercially available; however, most of these are single frequency impedance measuring devices. Two products are multi-frequency impedance devices. Specifically, the ImpediMed™ device uses 256 frequencies, and the Xitromm device uses 50 frequencies for sinusoidal current excitation in the range between 5 kHz and 1 MHz. While these devices are designed for total body analysis of extracellular fluid volume and total body fluid volume—and not for assessing the volume of a residual limb in a prosthetic socket—they can also support bioimpedance measurements on segmental regions of the body. The methods for determination of the fluid volume of a measured region, for all such instruments, are based on the Cole model, a stochastic model, a statistical model, or another modeling approach.

The assessment of the extracellular segmental volume of the lower residual limb of an amputee has unique challenges that none of these conventional bioimpedance measurement products can adequately address. The dynamic testing needed to understand the change in fluid volume of the residual limb requires a nearly real-time display of the changing fluid volume dynamics.

Currently, a Matlab™ software-based analysis of the Cole model, using the Xitron product as the bioimpedance measuring device, can provide a plot of extracellular fluid volume vs. time. At present, this method provides good experimental feedback for dynamic assessment of an amputee's changing residual limb volume, in near real time, when carried out in a clinical environment. Unfortunately, this method requires two computers, the Xitron device, and three engineers to operate and synchronize an experiment to achieve a usable result. Clearly, this conventional approach fails to meet the need for portability and lacks the capability to provide results in real-time, in a non-laboratory setting.

The problem that is experienced by amputees as the volume of their residual limb changes during the day and with activity is well-recognized. One approach that has been developed to address this issue to achieve a better fit as the volume of the residual limb changes (besides changing the number of socks on the residual limb) is to use a vacuum assist device (VAD), such as the ePulse™ system by Otto Bock. This vacuum assist device enables a patient to control a vacuum level applied to the socket cavity, which controls the force seating the residual limb within the prosthetic socket. Another approach that has been developed to address this issue of achieving a better fit as the volume of the residual limb changes is to adjust the volume of the socket and internal components. Examples include fluid-filled bladders (e.g., Active Contact System™, Simbex, Lebanon, N.H.; Volume Management Pads™, Ohio Willow Wood, Mount Sterling, Ohio), air-filled inserts (e.g., Pneu-Fit™, Prosthetic Concepts, Little Rock, Ark.; Pump-It-Up!™, Love Associates Inc, Batavia, N.Y.), and liners and sockets with electro-active, piezoelectric, or other types of "smart materials." It would be desirable to automate the control of these and other volume management devices by monitoring the volumetric change of the residual limb in the socket, and thereby automatically maintain a better fit between the prosthetic socket and residual limb as the volume of the residual limb changes, particularly with changes in the activity of the patient. It might also prove beneficial to automate the control of other prosthesis design features as the residual limb changes volume, for example, the socket suspension, or the action of the prosthetic foot, since these features affect the force delivered to the residual limb, and thus, affect the fluid transport process in the residual limb. Currently, no source of a signal indicative of changes in the volume of a residual limb is available that might be used for this purpose.

Accordingly, it is evident that a new approach is needed, which integrates all the essential features required in a single compact system and in a form so that a non-engineer can use the system to reliably access the dynamic changes in the volume of an amputee's residual limb in real-time.

The enhanced understanding achieved through such volume change measurement should reduce tissue breakdown risks and improve the quality of life of individuals with amputated limbs.

SUMMARY

This application specifically incorporates herein by reference the disclosures and drawings of the patent application identified above as a related application.

An exemplary method has been developed for using bioimpedance to measure volumetric changes of a residual limb of a subject over time, while the subject is wearing a prosthetic socket on the residual limb. The method includes the step of applying an alternating current to tissue of the residual limb, between two longitudinally spaced-apart points along the limb. A change in voltage at a plurality of points that are intermediate the two spaced-apart points is detected. Based upon the change in the voltage, Cole modeling is then used for determining a change in the volume of the residual limb over time.

A frequency of the alternating current is controlled to be within a frequency range from about 1 kHz to about 1 MHz.

Changes in the volume of the residual limb can be determined during periods of different types of activity, or during the diurnal period. The changes in the volume of the limb can be employed, for example, to determine if the prosthetic socket should be changed to provide a new prosthetic socket that better fits the residual limb of the subject. Further, the change in volume of the residual limb can be used to determine a non-essential fluid volume and an essential fluid volume, which aids a clinician in designing the new prosthetic socket. Further, measurement of the change in volume of the residual limb can be used to create a limb impression that correctly compresses the limb during the molding process, providing an objective way to set the initial socket volume to best match the essential fluid volume of the patient's limb. Also, the change in volume of the residual limb can be employed to determine a cause of a volume control problem for the subject.

It is also possible to use a signal indicative of the change in volume of the residual limb as a feedback signal to control a device, such as a vacuum assist device, which modifies the volume of the residual limb by applying a vacuum to the prosthetic socket. The feedback signal can automatically compensate for the change in volume of the residual limb as the subject engages in different activities.

It is also possible to use a signal indicative of the change in volume of the residual limb as a feedback signal to control a device, such as a fluid-filled insert, which modifies the volume of at least one of the socket and internal components by adjusting the fluid volume in the insert or by adjusting an applied voltage to a line comprising an electro-active material. The feedback signal can automatically compensate the volume of the fluid-filled (or other type of) insert for the change in volume of the residual limb as the subject engages in different activities.

It is further possible to use a signal indicative of the change in volume of the residual limb as a feedback signal to control a device on the prosthesis, such as a micro-controlled foot/ankle, which modifies the prosthetic fit, gait, and/or performance. The feedback signal can automatically compensate the action of the foot/ankle for the change in volume of the residual limb as the subject engages in different activities.

The signal indicating the change in volume of the residual limb can also be used to assist a clinician in determining an appropriate treatment of the subject, and/or to reduce volume fluctuations of the residual limb.

Another aspect of the present novel approach is directed to a system for assessing volumetric changes of a limb of a subject, while the subject is wearing a prosthetic socket. The system includes a first current electrode and a second current electrode that are configured to couple electrically to tissue respectively at a proximal position and a distal position along a longitudinal axis of a limb. A plurality of voltage electrodes in the system are configured to couple to tissue of the limb at spaced-apart positions that are intermediate the first and the second current electrodes. An alternating current source is coupled to the first and the second current electrodes and produces an alternating current for injection into tissue of the limb. A processing device is coupled to the voltage electrodes and senses a voltage across pairs of the plurality of voltage electrodes, producing a signal indicative of a change in the volume of the limb over time. Further details of the system and its function are generally consistent with the steps of the method discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 3A:
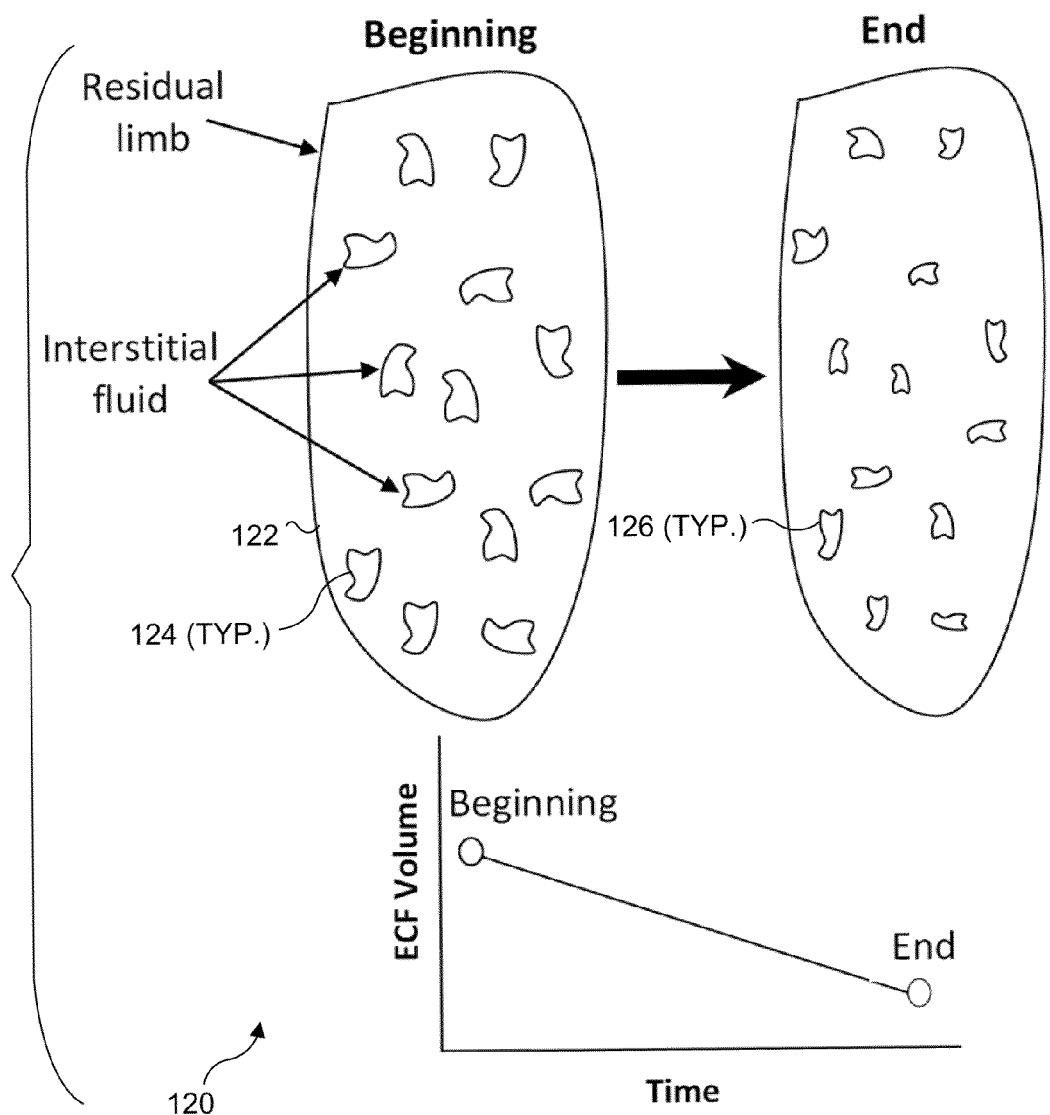
FIG. 3A is a schematic drawing illustrating the volume change in a residual limb while a subject is standing, due to an increase in interstitial pressure, which causes interstitial fluid to be expelled, reducing the extracellular fluid (ECF) volume, as indicated on a graph included in the Figure.
Figure 3B:
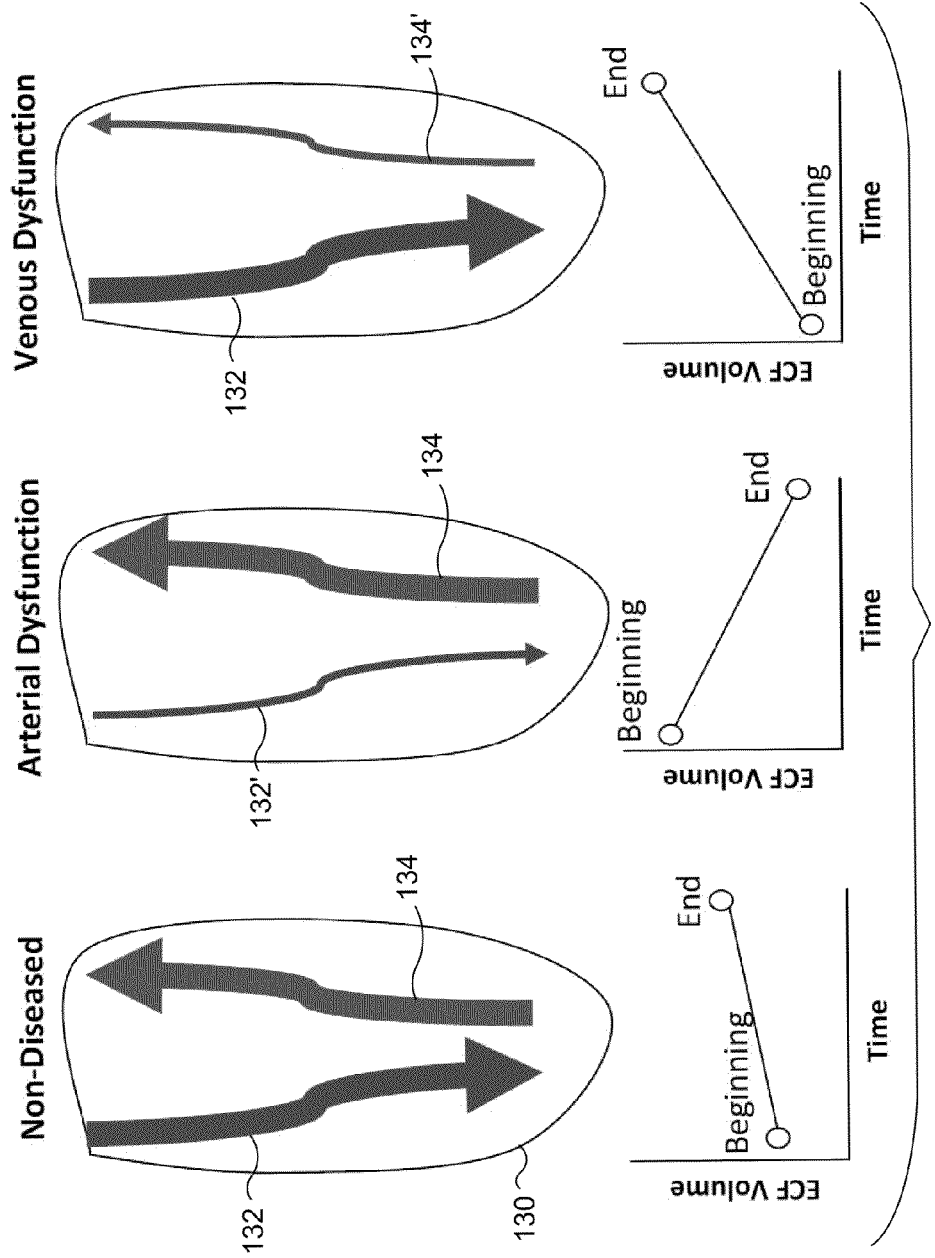
Figure 4:
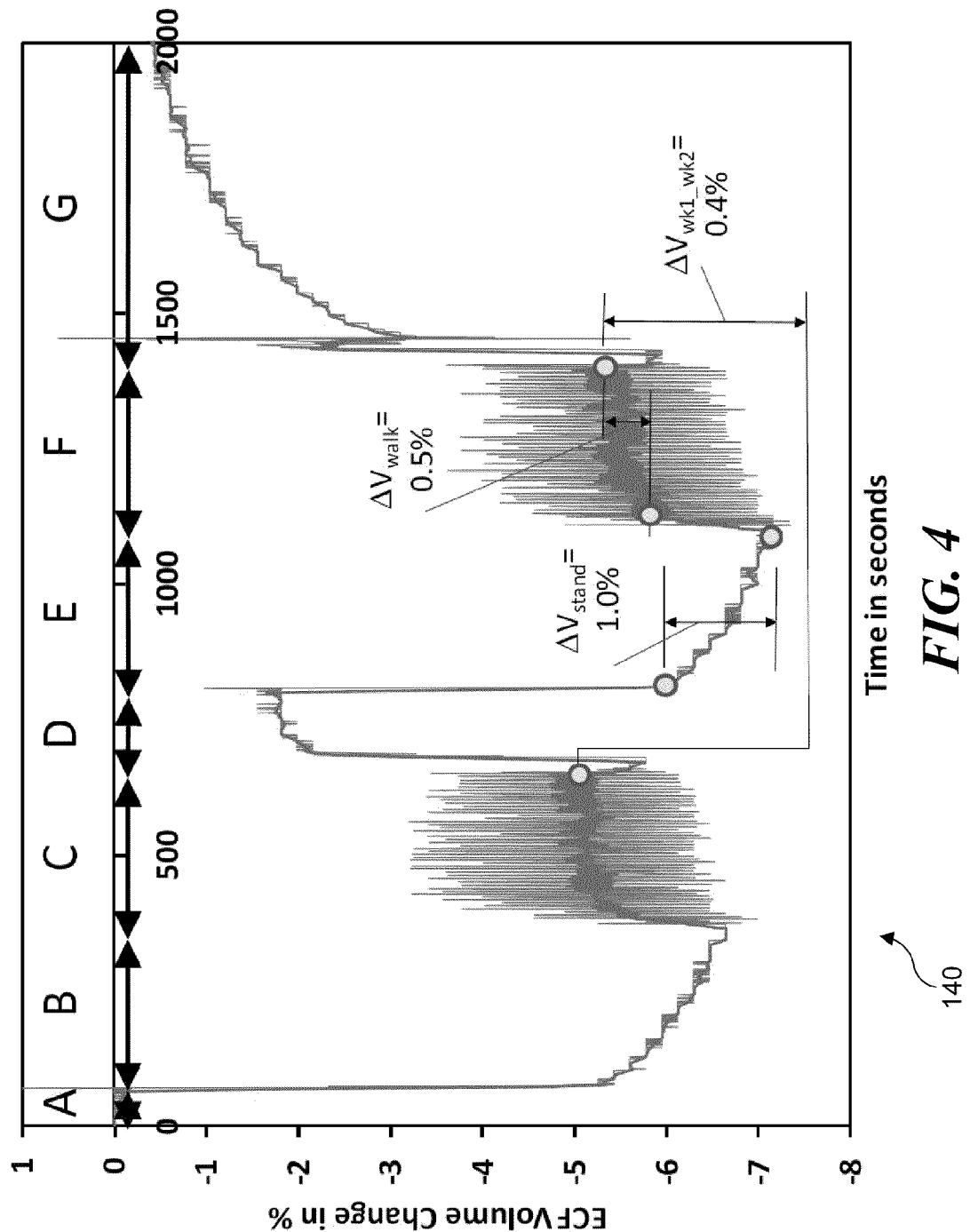
Figure 5A:
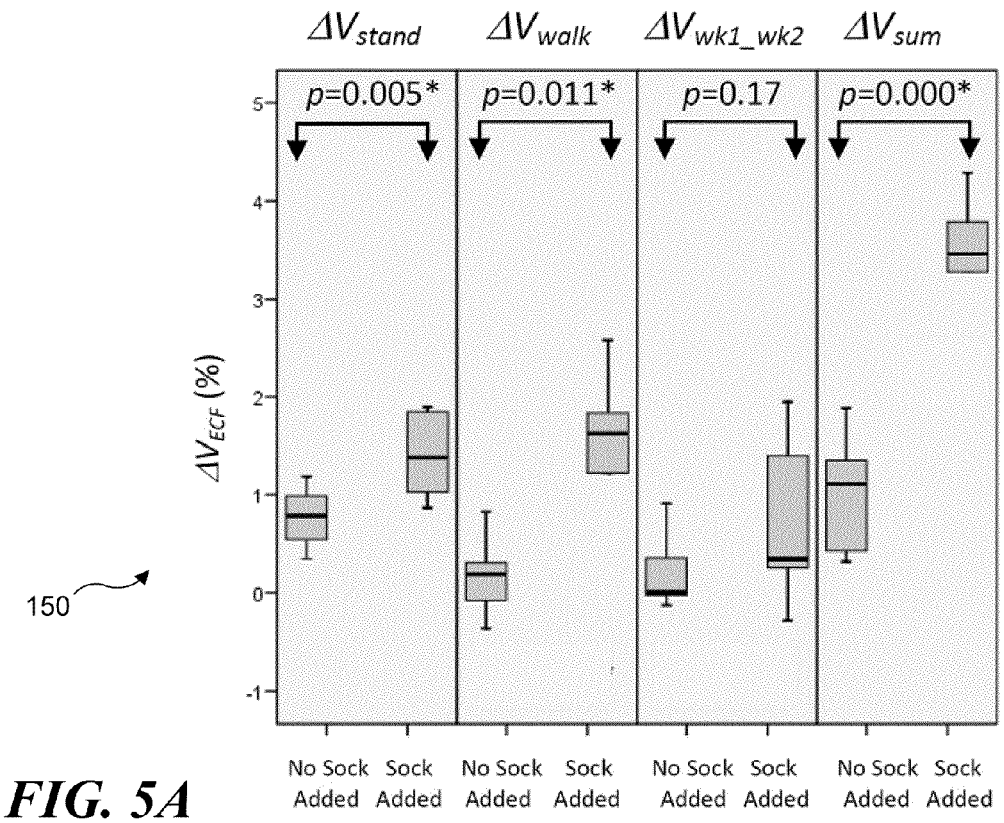
Figure 5B:
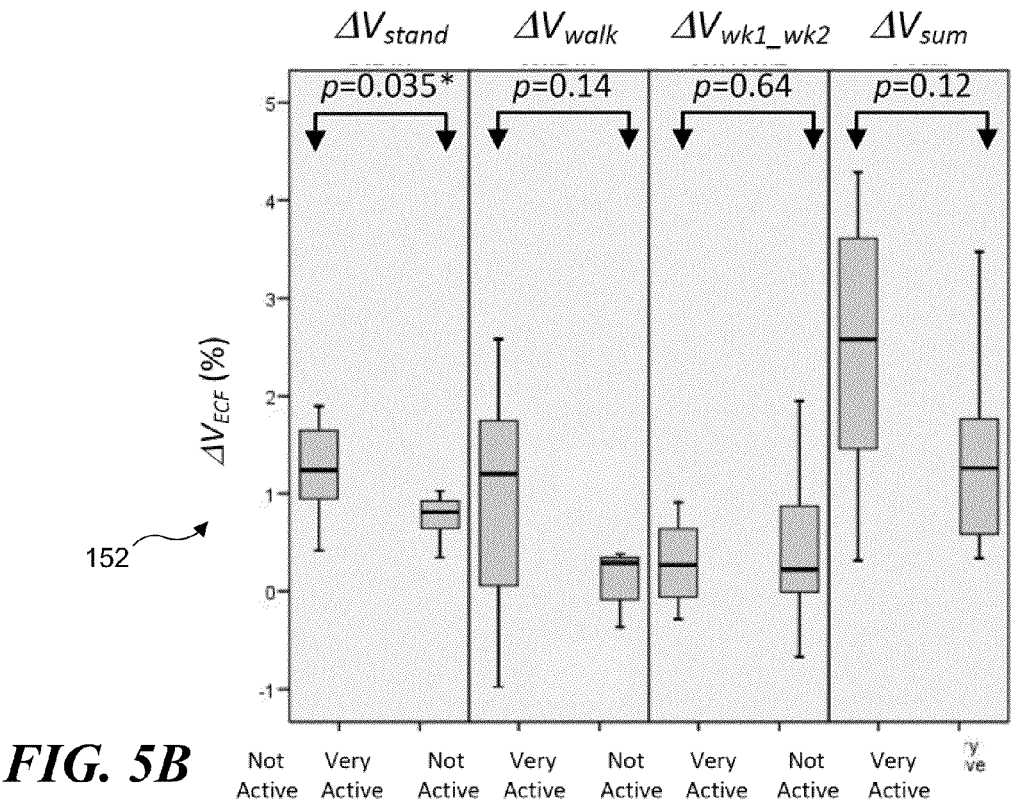
Figure 6B:
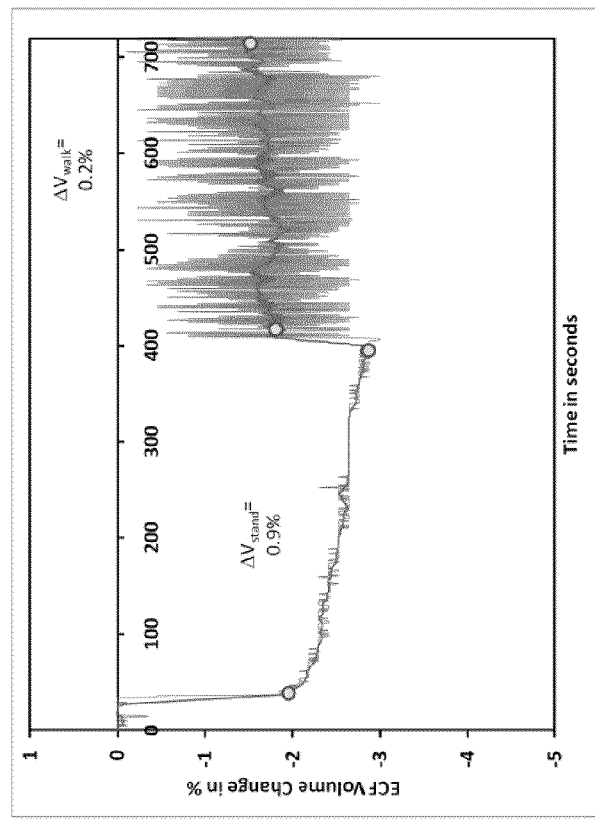
Figure 6A:
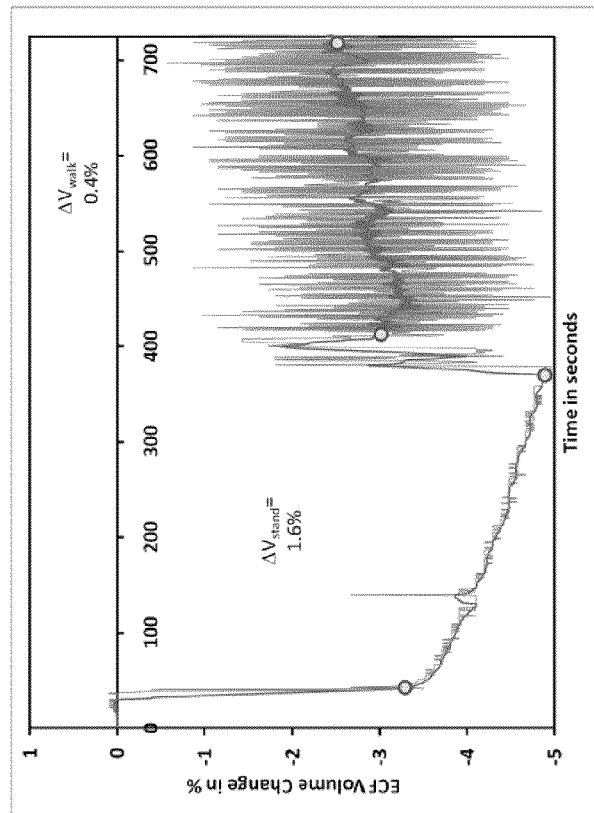
Figure 7B:
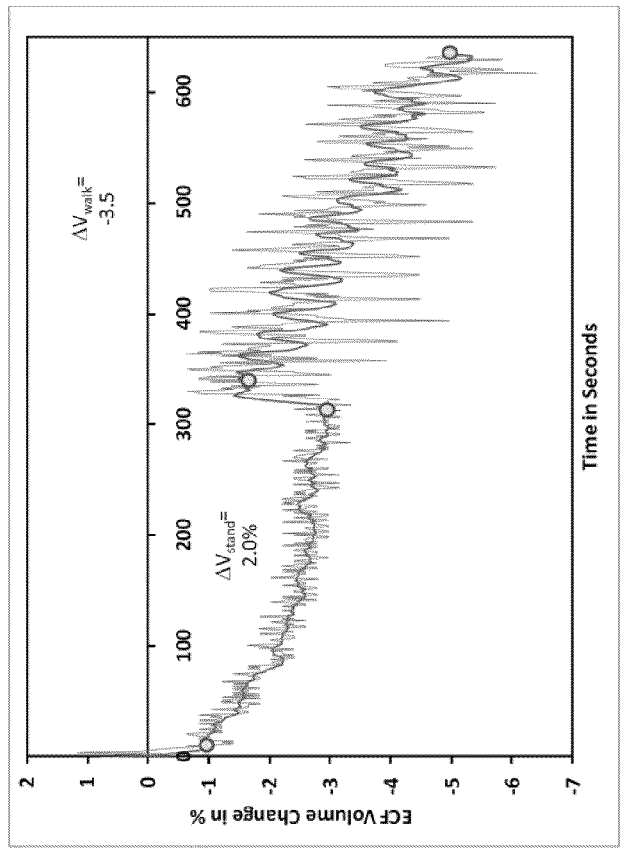
Figure 7A:
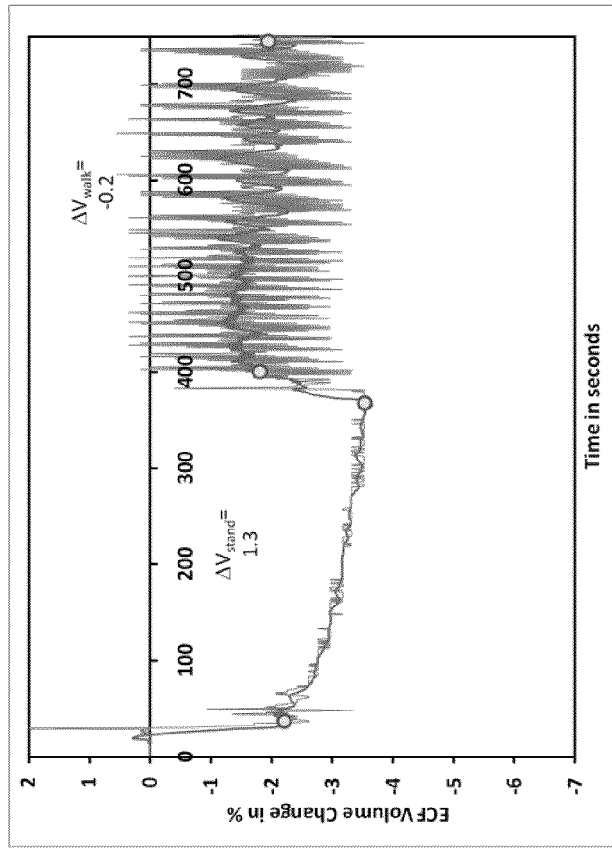
Figure 8:
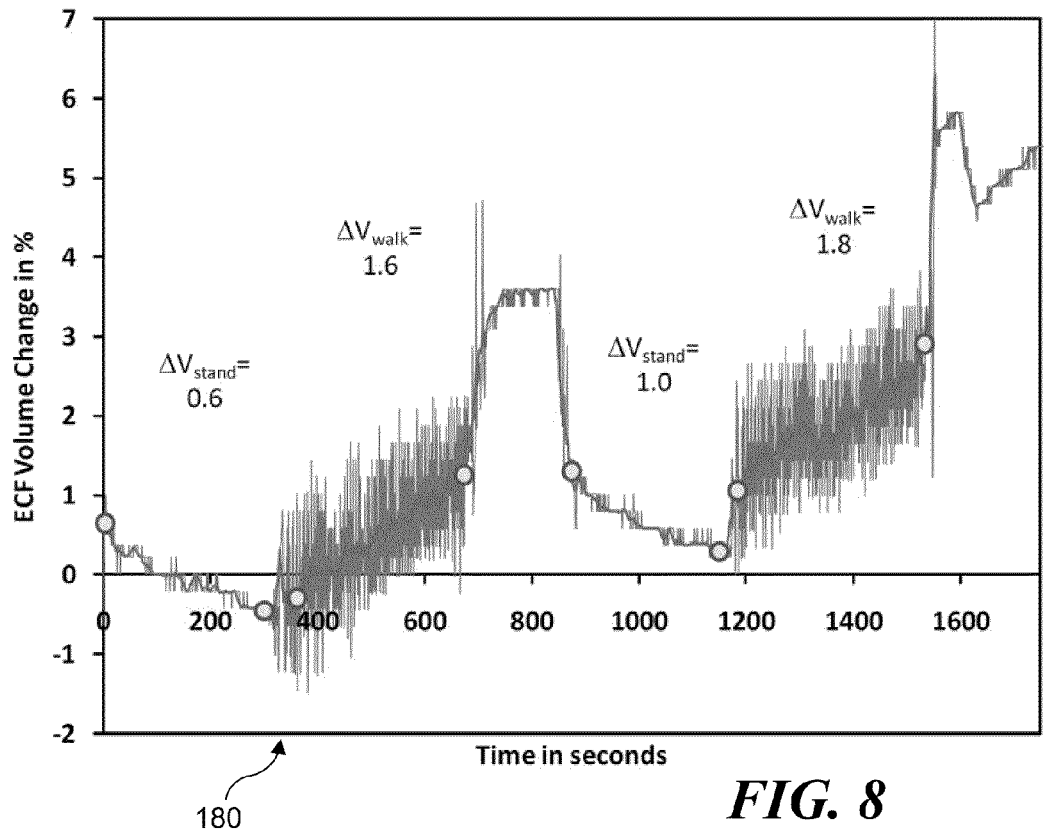
Figure 9:
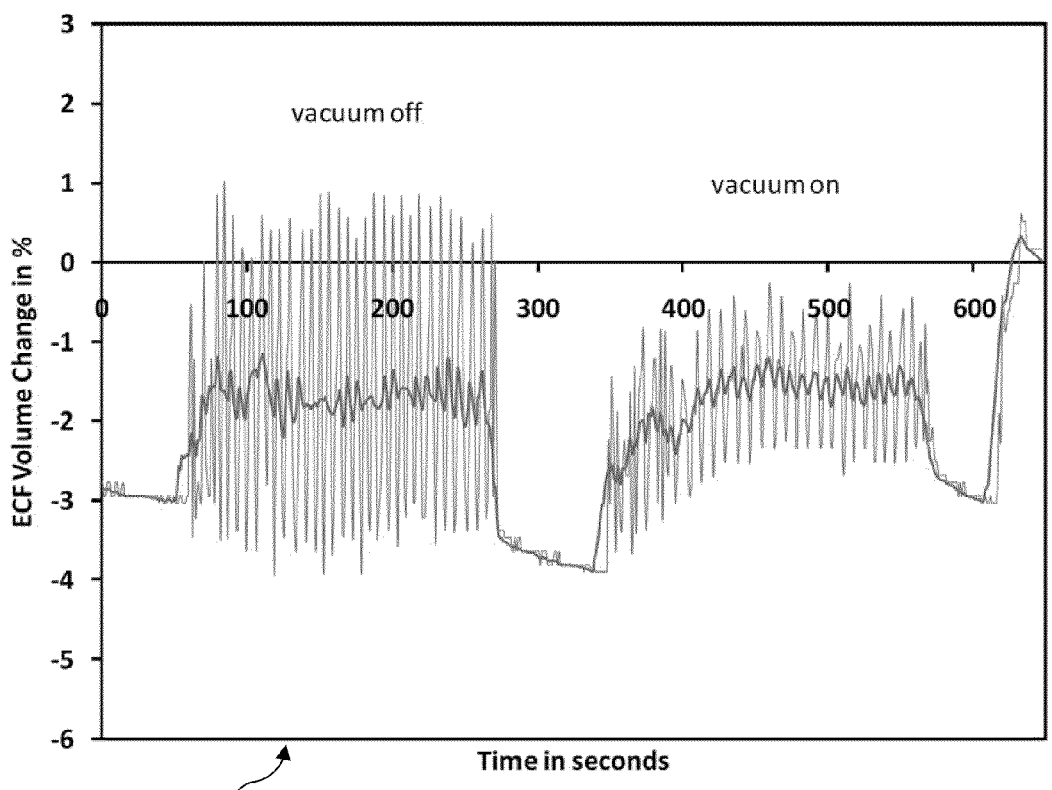
Figure 10:
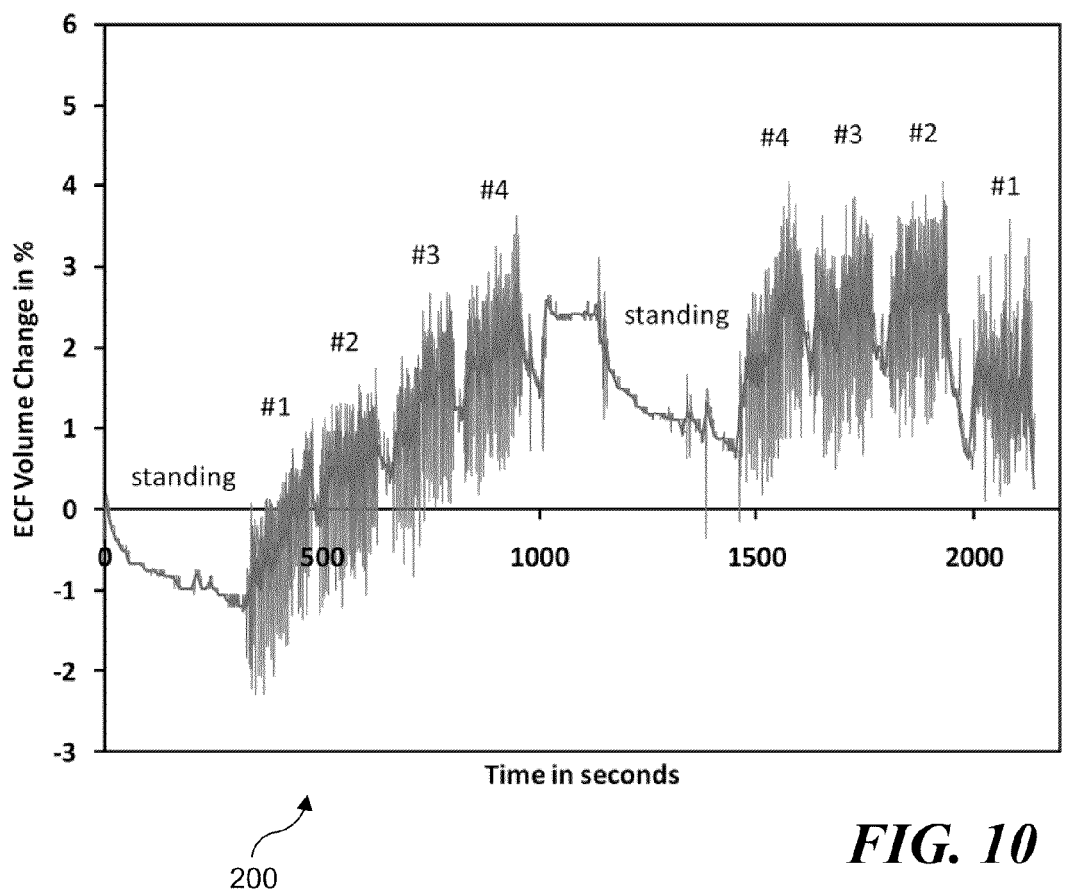
Figure 11:
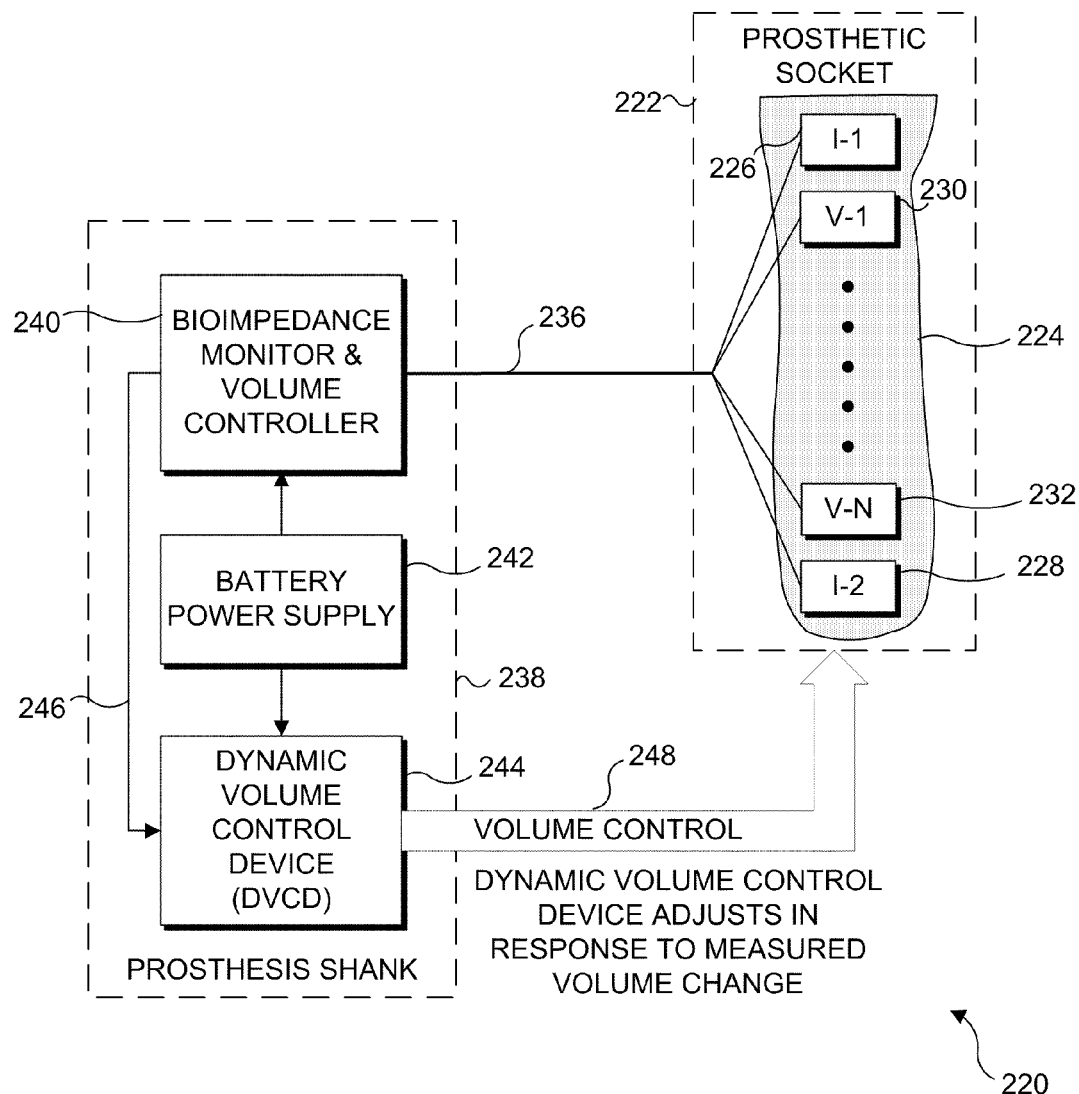
Figure 12:
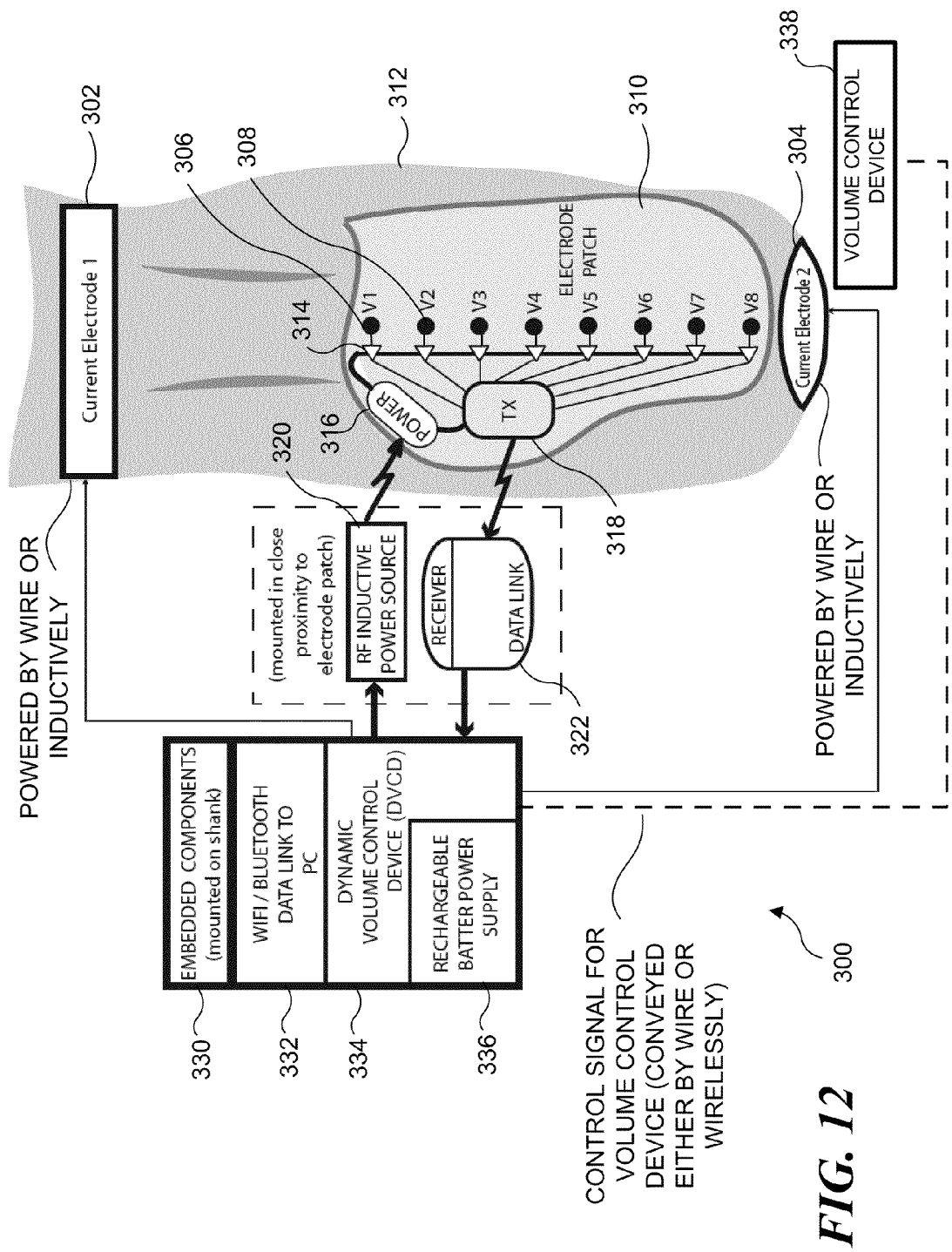

FIG. 3B includes three schematic drawings of residual limbs, respectively showing limb volume change during walking (after a 5-minute standing interval) for a non-diseased limb, a limb of a subject suffering arterial dysfunction, and a limb of a subject suffering venous dysfunction, along with corresponding graphs showing the change in ECF volume for each limb over the time of walking;

FIG. 4 is a graph showing % ECF volume change over time as determined by bioimpedance results, for the limb of a healthy subject, for intervals of standing and walking, and indicating the change between the end of a first walking interval and the end of a second walking interval;

FIGS. 5A and 5B are boxplots respectively showing changes in volume response variables for no-sock adder vs. sock adder subjects, and for non-active vs. very active subjects;

FIGS. 6A and 6B are graphs showing % ECF volume changes over time, for standing and walking segments of a subject, respectively, at six months after the amputation of the limb, and at 12 months after the amputation;

FIGS. 7A and 7B are graphs respectively showing % ECF volume change over time, for standing and walking segments of a subject suffering from congestive heart failure while on a healthy diet, and after three weeks of eating a high salt content diet;

FIG. 8 is a graph showing % ECF volume change over time, for standing and walking segments by a regular vacuum assist user (Case A);

FIG. 9 is a graph showing % ECF volume change over time, for walking segments, with the vacuum assist off and on (typical of three subjects—Cases B, C, and D);

FIG. 10 is a graph showing % ECF volume change over time, for standing and walking segments, with successively higher settings of the vacuum level applied (for the subject of Case D);

FIG. 11 is a functional block diagram illustrating the use of bioimpedance monitoring to control a dynamic volume control device (DVCD) used with a prosthetic socket fitted to a residual limb; and FIG. 12 is functional schematic diagram illustrating another exemplary embodiment for measuring bioimpedance using a flexible biocompatible electrode patch that is applied to a residual limb and inductively wirelessly receives power to energize amplifiers disposed on each voltage electrode, and uses wireless data link to convey voltage signals from the amplifiers to an adjacent receiver that is coupled to components for determining the volume of the residual limb (and optionally, wirelessly providing a feedback signal to modify either the volume of the cavity in a prosthetic socket or control the volume of the residual limb using a vacuum applied to the socket).

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Exemplary Instrumentation for Measuring Bioimpedance
Objective—Overview

One of the goals of the present novel approach is provide an instrument or tool that can be used to quickly and quantitatively monitor a residual limb diurnal volume change, as well as changes in volume related to subject activity. This tool can thus be used to identify a primary source or cause of the volume change, so that the physician can more readily prescribe appropriate treatment. It is envisioned that a clinician might use this tool during a short evaluation of a patient (e.g., taking only about 30 minutes) and fit of a prosthetic socket, so that the patient might be immediately provided with the results of the evaluation and interpretation at the end of that session. Further, it is expected that the objective data produced by this tool can readily be incorporated into a clinical fitting routine for sockets, in contrast to the more subjective determination of fit that is currently typically employed.

Regular use of this tool on at-risk patients will potentially enable detrimental volume change trends to be identified early, before tissue injury occurs. Practitioners thus have reason to be excited about the development of this instrument.

Preliminary data obtained during the development of this instrument are very encouraging in indicating that these and other goals will be met. In a study on subjects with trans-tibial amputation, an early exemplary embodiment of this instrument effectively identified subjects who needed to add stump socks to accommodate their diurnal residual limb volume loss compared to those who did not. Individual case analysis also provided insight. For example, links were found between cardiac insufficiency for specific patients, and the volumetric change of the residual limbs in those patients. Consistently, changes in the volumetric data were observed when a person with a recent amputation transitioned from a residual limb reducing in volume over time, to a stable limb. In another case, when a subject with cardiac insufficiency drastically changed his diet by adding salty foods, the effects of the dietary change were readily evident in the volumetric change data.

These results are exciting and highly encouraging, particularly in view of more recent refinements to the instrumentation. It appears that this tool may find use as a regular installed system on the prosthetic devices used by amputees and when used in combination with currently available VADs, may enable the automatic dynamic control of the vacuum assist level applied, to achieve continuous improved fit between the socket and the residual limb in response to volume changes of the limb while the subject engages in different types of activity.

Bioimpedance Measurement

A bioimpedance measurement modality is used for this assessment. Bioimpedance is a noninvasive means for assessing extracellular fluid (ECF) volume and intracellular fluid (ICF) volume within living tissue. It is the ECF volume that is the primary source of limb volume fluctuation in amputee prosthesis-users. ECF includes blood and interstitial fluid. Interstitial fluid is plasma that enters and leaves the interstitial space. Bioimpedance analysis has typically been used as a tool principally for body composition/body fat analysis and in the assessment of fluid imbalance in hemodialysis patients. The present approach is thus novel in the use of bioimpedance for measuring change in the volume of residual limbs fitted with prosthetic sockets. It is envisioned that this instrument can be extended to other areas of rehabilitation, including orthotics, seating, and foot care where soft tissue volume change is of clinical interest.

Figure 1:
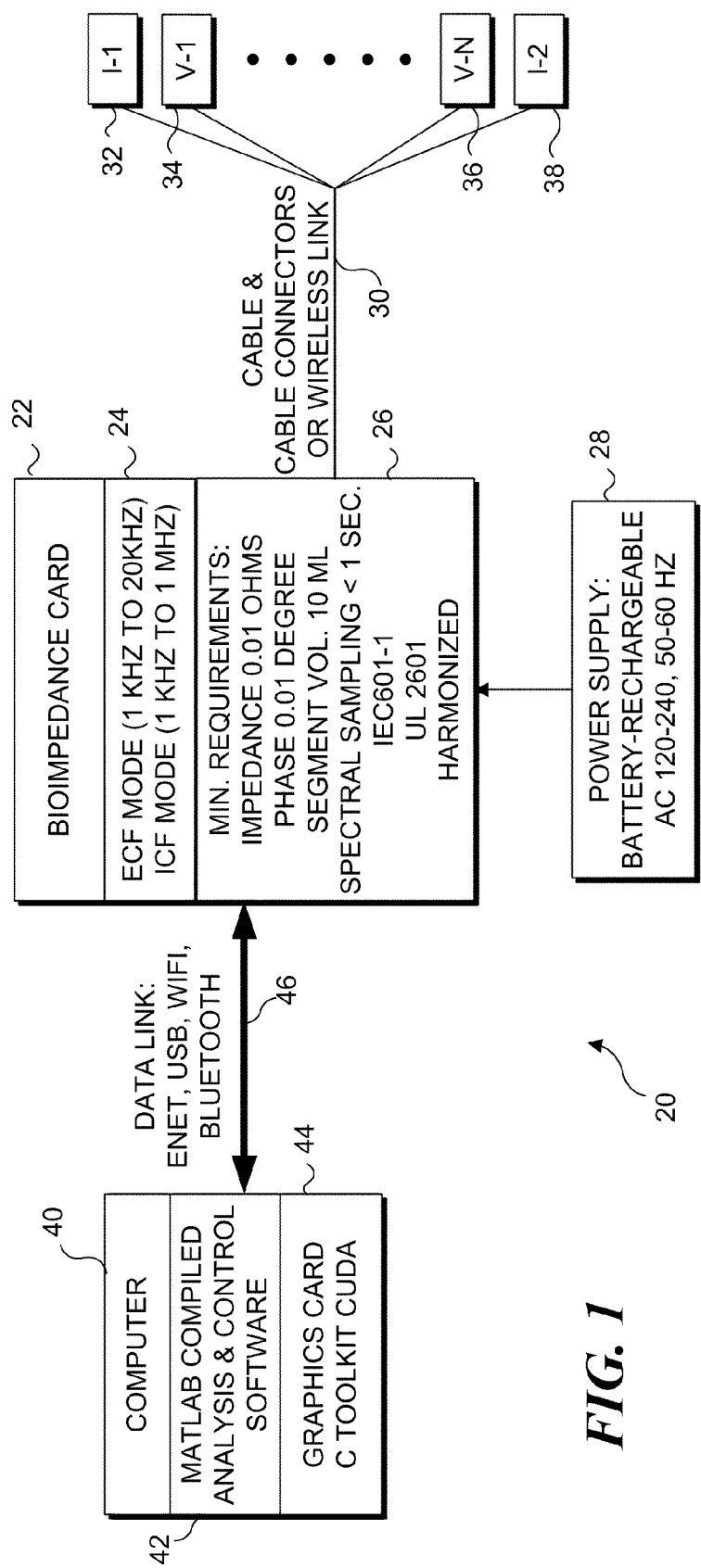
FIG. 1 is a functional block diagram illustrating components of an exemplary bioimpedance for real-time segmental limb volume assessment.

The function of bioimpedance analysis is to measure biological conductivity. Biological conductivity in the residual limb occurs primarily through fat-free tissues and fluids, as opposed to bone or adipose tissue. It is the changes in the fat-free tissues and fluids, particularly the ECF, that cause amputee diurnal socket fit problems. To conduct a bioimpedance test, a very low electrical current (<700 µA) is injected into the residual limb through two outer pair current electrodes 32 and 38, while voltage potential is measured across two or more inner voltage electrodes, such as voltage electrodes 34 and 36, as shown in FIG. 1. The current and voltage electrodes are coupled through cables and cable connectors 30 to a bioimpedance controller 20. An alternative approach is to couple the electrodes to the controller using a wireless connection, such as Bluetooth, or WiFi (without any implied limitation). In this exemplary embodiment, the bioimpedance controller includes a bioimpedance card 22, a control 24 to selectively operate in an ECF mode (by injecting current at a frequency range from 1 kHz to 20 kHz), or in an ICF and ECF mode (by injecting current at a frequency range from 1 kHz to 1 MHz). In this embodiment, current is injected over a range of frequencies (between about 5 kHz and about 1 MHz) each second. The lower frequencies tend to travel through the ECF of the residual limb, since cell membranes are not well-penetrated by low frequency signals. At high frequencies, however, current travels through both the ECF and ICF. Using data at different frequencies in a modeling strategy known as Cole modeling, the ECF resistance can be calculated, as discussed in more detail below. ICF can also be calculated.

An alternative to the cable and cable connectors 30 is a wireless connection between the voltage sensing electrodes and bioimpedance electronics. A wireless connection offers to the user the capability to remove the prosthesis without removing the electrodes or disconnecting the cable connectors coupled to them. For long-term use (days or weeks), environments where frequent prosthesis donning and doffing are necessary, or when cables are inconvenient, the wireless connection is advantageous. To achieve a wireless connection to the voltage sensing electrodes, small voltage sensing electrodes, amplifiers, power receiver, and data transmitter are embedded within a flexible non-conductive pad attached to the skin. The electronic components in the pad communicate wirelessly with a nearby inductive power source and a data receiver, which can be disposed in the prosthetic socket, and in turn, attaches to the bioimpedance card. A block 26 indicates that the minimum impedance required for the measurement circuit is 0.01 ohms, the phase is 0.01 degrees, the segment volume (i.e., the segment between voltage electrodes) is about 10 ml, and the spectral sampling occurs in less than 1 second. A power supply comprising rechargeable batteries 28 provides the power for the bioimpedance controller. A data link 46 comprising either an Ethernet cable, a universal serial bus (USB) link, or a wireless radio frequency link, e.g., either a WiFi signal, or a Bluetooth signal, conveys data related to the change in volume of the limb being monitored to a computer 40 that is running MatLab™ compiled analysis and control software 42, and which includes a graphics card with C toolkit Compute Unified Device Architecture (CUDA) 44. The computer can display real-time changes in the ECF or ICF volume of a limb in the form of a graph (like those discussed below) during different activities of the subject, such as standing and walking.

Figure 2A:
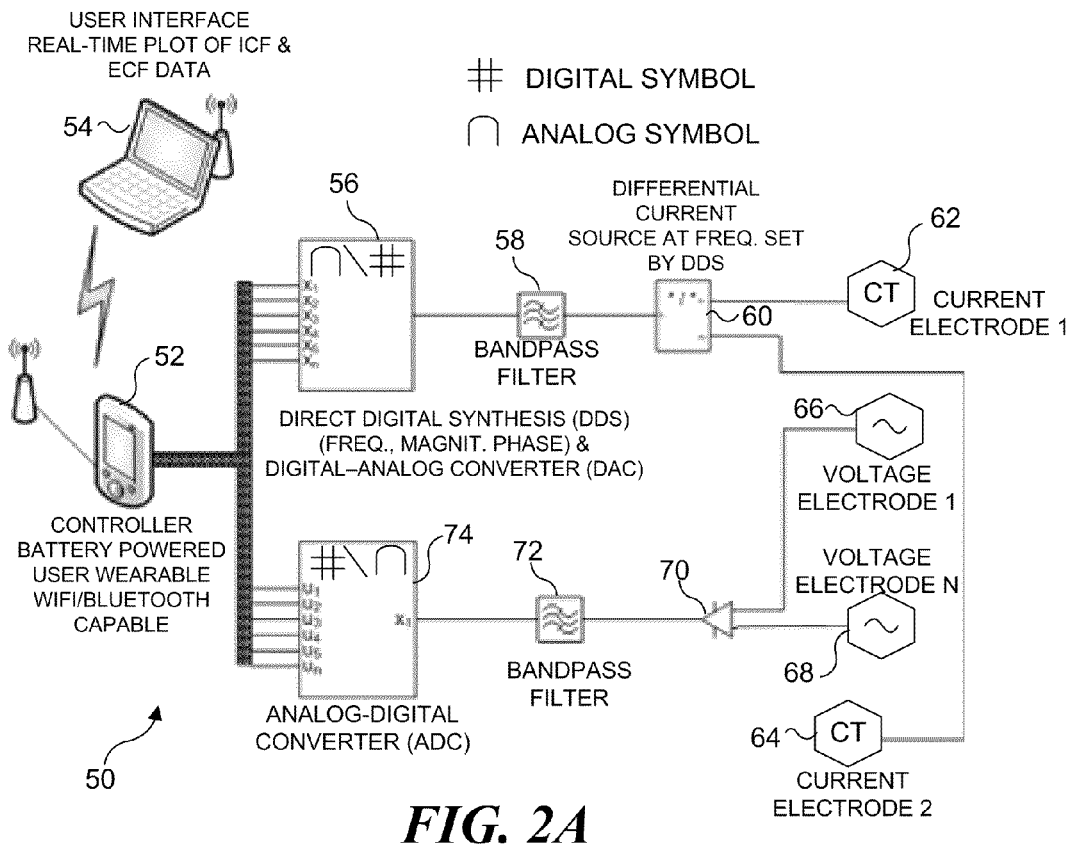
FIG. 2A is block diagram showing further functional details of an exemplary bioimpedance device for multi-frequency real-time analysis and display of both ECF and ICF segmental volumes.

FIG. 2A illustrates further details of an exemplary bioimpedance measurement system 50, which includes a controller 52 that is battery powered and sufficiently small to be user wearable (or attached to the shank of the prosthesis) and which can communicates wirelessly (using WiFi or Bluetooth) with a laptop 54 that can display the real-time ICF and ECF volumetric change data. While not separately shown, controller 52 can include a storage such as a memory chip or card on which volumetric change data for a period of time (e.g., for 24 hours or more) can be stored, so that the data can be uploaded via the wireless communication on demand when desired. Controller 52 is coupled to a direct digital synthesis (DDS) card 56 with control of frequency, magnitude, and phase, and which includes a digital-analog converter (DAC—not separately shown). Current signals at the desired frequencies are applied to a bandpass filter 58, which passes a desired band of frequencies to a differential current source 60, at the frequency set by the DDS. This current is injected into the limb of the subject by current electrodes 62 and 64. Voltage electrodes such as voltage electrodes 66 and 68 (at least two in number) are applied to the limb of the subject, and the differential voltage sensed between two adjacent voltage electrodes is applied to a differential amplifier 70, which produces a signal that is input to a bandpass filter 72. The resulting filtered signal is input to an analog-digital converter (ADC) 74, which converts the analog voltage level to a corresponding digital signal that is input to controller 52 for processing to determine volume change.

Figure 2B:
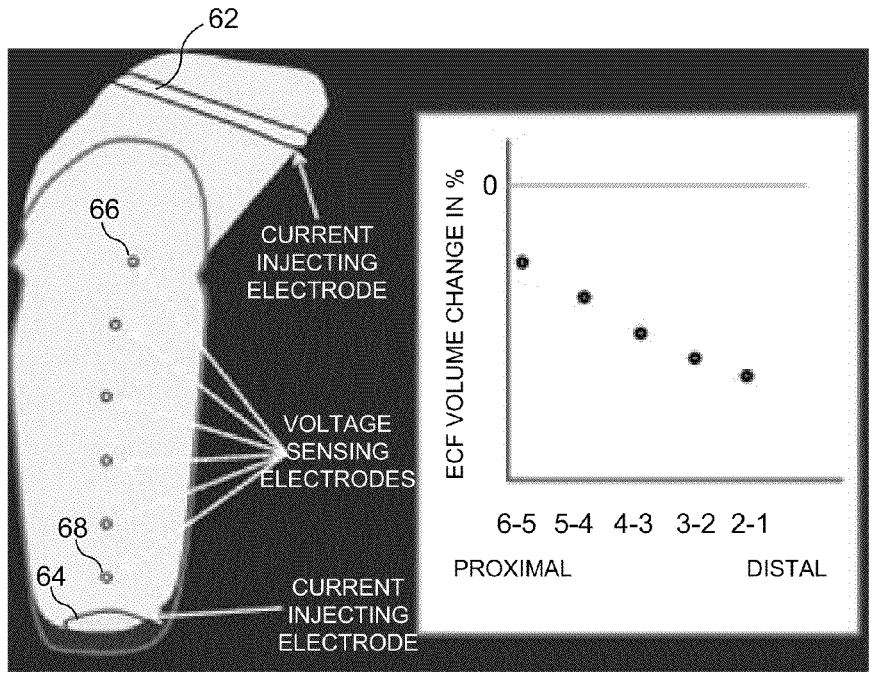
FIG. 2B is a schematic illustration and corresponding graph showing the disposition of two current injecting electrodes, and a plurality of voltage sensing electrodes that are applied to a subject's skin, so that volumetric changes between voltage sensing electrode pairs can be monitored, as shown in a corresponding graph.

As shown in a schematic view 80 in FIG. 2B, current electrode 62 can comprise a band with an electrically conductive undersurface that is affixed by adhesive to a proximal portion of the limb of a patient. Current electrode 64 can be a cushioned flexible electrically conductive sheet disposed in the bottom of the socket so that it contacts (but only with a comfortable level of force) the lower end of the residual limb while the socket is being worn, or may be adhesively affixed to the limb proximate to its lower end, if excessive scarring precludes contact with the end of the residual limb. Voltage sensing electrodes (six are used in this exemplary illustration), such as voltage electrodes 66 and 68, can be applied at different points along the longitudinal portion of the residual limb, intermediate between the points where current electrodes 62 and 64 contact the limb. Two or more voltage electrodes (where more is generally preferable) can be used. It is contemplated that these electrodes can be adhesively attached to the posterior surface of the limb; however, an alternative approach may be to provide tack-like points on the electrodes so that they point-press the tissue of the limb and thus have a better contact with the limb. The electrodes may be MEMS chip-electrodes with arrays of approximately 400-nanometer conductive needles to reduce the impedance at the skin interface without causing discomfort or increasing the risk of infection or bio-fouling of the electrode skin interface. The graph in this Figure illustrates an exemplary % ECF volume change in the segments between adjacent voltage electrodes from the proximal to the distal end of the limb, where each segment is defined as the transverse (geometric) "slice" of the limb disposed along the longitudinal axis of the limb between adjacent voltage electrodes.

Figure 2C:
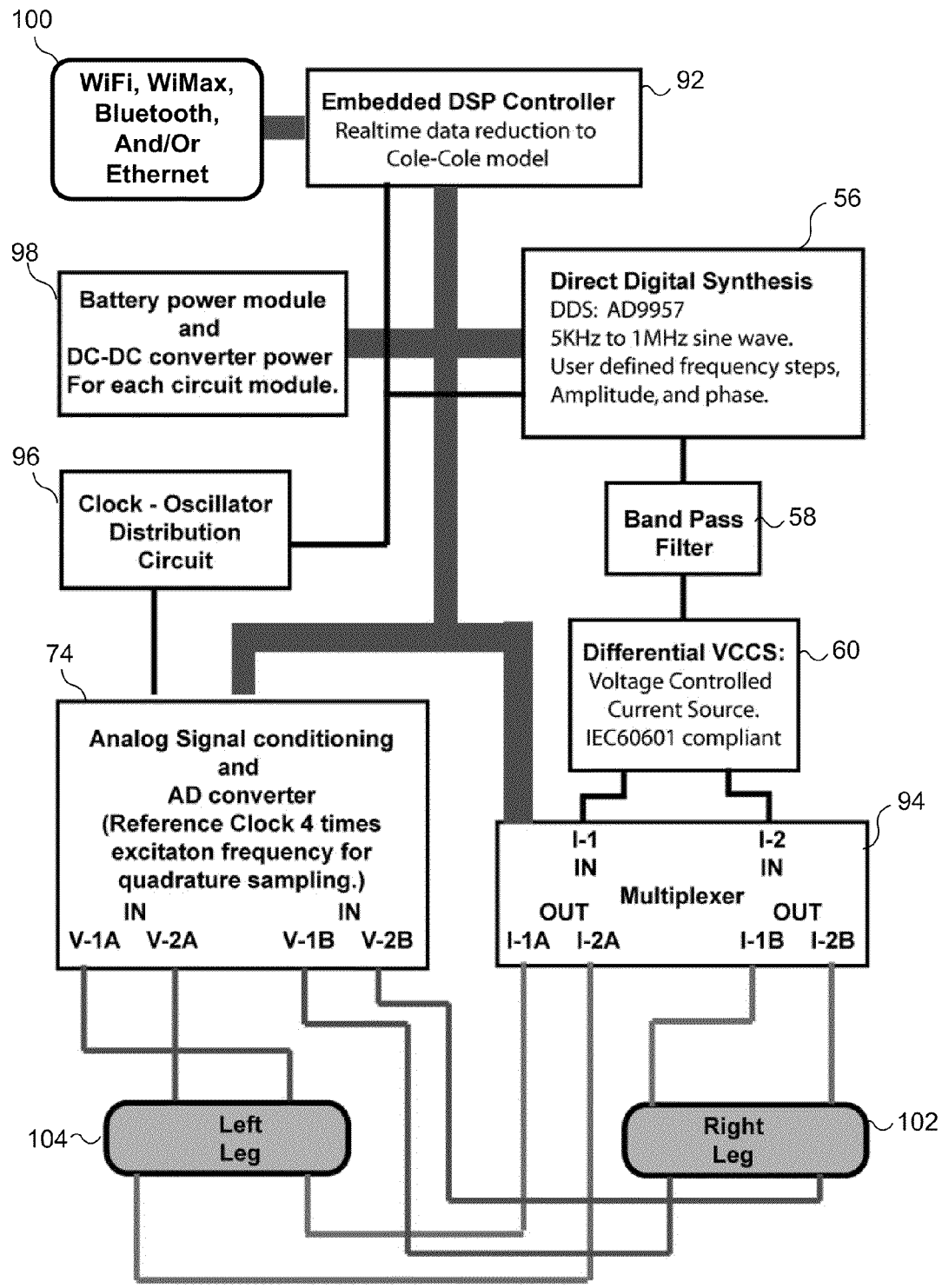
FIG. 2C is block diagram illustrating exemplary components for lower limb bioimpedance assessment of two legs in real time.

An alternative exemplary embodiment 90 for use in monitoring changes in volume in a residual limb and contralateral limb is shown in FIG. 2C. Many of the components are the same as in the exemplary embodiment of FIG. 2A. However, embodiment 90 includes an embedded digital signal processor 92 for implementing the real-time data reduction in accord with the Cole model, a multiplexer 94 for selectively switching the applied current signals to be injected to either current electrodes on a right leg 102 or to current electrodes on a left leg 104, a clock—oscillator distribution circuit 96, a battery power module and DC-DC converter power supply 98 for each circuit module, and a WiFi and/or Ethernet interface 100, for coupling the output signals to an external computing device, for storage and/or display of the volumetric changes.

Figure 2D:
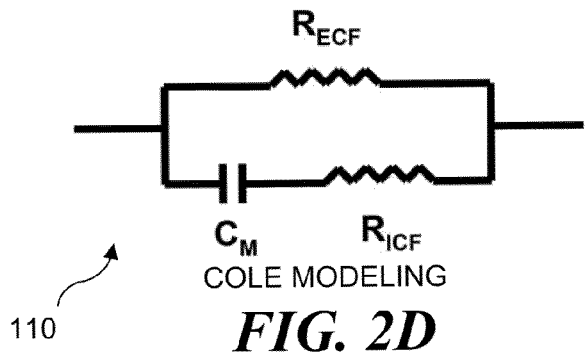
FIG. 2D is an electric schematic for the Cole model, wherein tissue is modeled as extracellular fluid resistance, in parallel with intracellular fluid resistance and cell membrane capacitance.

As indicated in FIG. 2D, Cole modeling 110 is used during the bioimpedance measurements and comprises an equivalent electrical circuit that consists of an extracellular resistance ($R_{ECF}$), intracellular resistance ($R_{ICF}$), and cell membrane capacitance ($C_m$). Nonlinear weighted least-squares curve-fitting applied to the multi-frequency impedance spectrum is used to extrapolate $R_{ECF}$ and $R_{TOT}$ at the low and high-frequency limits. Volume as a function of resistance is defined by:

$$V = \frac{\rho L^2}{R}$$

where V is limb fluid volume, R is the fluid resistance, L is the limb segment length, and $\rho$ is the specific resistivity of the biofluid in the limb. For segmental bioimpedance analysis (assessment within a limb segment of the residual limb), mixture theory can be used to account for the presence of non-conducting elements within the limb:

$$V_{ECF} = \left(\frac{1}{1000}\right)\left(\frac{\rho_{ECF} C}{R_{ECF}}\right)^{\frac{2}{3}} \frac{L^{\frac{5}{3}}}{(4\pi)^{\frac{1}{3}}}$$

where the limb segment is assumed to be a cylinder with an average circumference C and length L.

Assessments conducted in the lab have demonstrated that bioimpedance analysis has sufficient signal-to-noise ratio and sensitivity for prosthetic application. The instrument noise (repeatability, drift) was less than 0.014%/hr. Changes during 5-minute standing intervals on amputee subjects averaged 1.1%, and changes from the beginning to end of a 30-minute activity session averaged 2.3%. Thus, for prosthetic applications, the measurements of clinical interest are far greater than the noise in the instrument.

An exciting result from an initial study on 15 subjects with trans-tibial amputation was the suggestion that measurements conducted during a 30-min session reflected diurnal volume changes encountered over the entire day. This result is important in terms of clinical utility of the instrument. Rather than relying exclusively on subjective patient verbal comments, visual inspection of the limb, and the slow process of feedback from each prosthesis or sock modification, a practitioner can now benefit from a quantitative objective assessment. Much time and energy can thus be saved.

Providing insight into the source of limb volume change is a unique potential application of bioimpedance analysis. It is unique in that all other means used for residual limb volume assessment (volume displacement, magnetic resonance imaging (MRI), computer tomography (CT), ultrasound, laser and optical scanners) are applied after the socket is doffed, i.e., removed. It is the time while the residual limb is actually within the prosthetic socket that is of interest, not after doffing. In-socket measurement is a unique capability of bioimpedance measurement, since it provides an opportunity to assess changes in the volume of the residual limb while the socket is being worn and the subject is active in carrying out designated or normal activities. In contrast, a subject is stationary within an imaging apparatus, when MRI, CT, ultrasound, laser or optical scanning is used. Thus, these other means do not enable measurement of limb volume to occur during activity. This limitation of conventional imaging or scanning paradigms makes it difficult to investigate the physiological sources of volume change. In contrast, bioimpedance analysis does not have these limitations. Pursuing identification of the sources of limb volume change is thus a unique and exciting application of this novel instrument.

By using data from a 30-minute bioimpedance test to determine the source of a volume fluctuation, a clinician can not only prescribe a better treatment for a patient, but can do so immediately. Patient changes can also be tracked, and the need for intervention identified early before limb tissue breakdown occurs. Based on the changes in volume determined using bioimpedance measurement, a clinician can assess the changes in volume of the limb to determine if the prosthetic socket used by the subject should be changed to provide a new prosthetic socket that better fits the residual limb of the subject, or determine the cause of a volume control problem in the subject, or determine an appropriate drug treatment or therapy for the subject. For a recent amputee, the measurement of volume change can be used by a clinician to determine the best post-operative treatment to facilitate limb adaptation to a socket, or to select the best physical therapy that will control edema and reduce limb volume fluctuation.

To investigate sources of limb volume change, extensive testing has been conducted in a clinic on individuals with trans-tibial amputation during different activities (sitting, standing, and walking), while making note of their health status and medical history, as well as measuring their arterial and venous functional status. It is the changes in volume during and between such activities that reveal the individual's main sources of limb volume change. Measured arterial and venous functional assessments, health status, and medical history are linked with bioimpedance data. For example, it is expected that arterial dysfunction is reflected as a negative limb volume change during walking. A schematic illustration of this effect is illustrated in FIG. 3B. As shown in the left panel of this Figure, in a non-diseased or normal subject, a limb 130 has an arterial flow 132 and a venous flow 134 that are nearly equal. However, unlike normal subjects, those without sufficient arterial drive or without an adequate arterial vascular plexus experience inadequate fluid transport from the arterial side into the interstitial space, as shown as a reduced arterial flow 132' in the middle panel of FIG. 3B. In other words, the mechanism for fluid transport out of the limb (interstitial to venous) is intact, but the means for fluid transport into the limb (arterial to interstitial) is insufficient. As a result, the limb reduces in volume appreciably during the 5-minute walking segments of the 30-minute test, instead of enlarging slightly, as it does in non-diseased subjects. This condition is shown in a graph 140 in FIG. 4.

Venous dysfunction is also expected reflected in the walking activity test results. Because the capability to remove interstitial fluid from the limb is compromised, as indicated by a reduced venous flow 134' in the right panel of FIG. 3B, these subjects are expected to experience much limb enlargement compared to normal, non-diseased subjects during walking, after 5 min. of standing. Note that the lymphatic system is considered to be part of the venous system in this analysis, since the performance of the two systems is almost always tightly linked.

It is expected that subjects who are relatively inactive (low K level ($K_1$, $K_2$)) will have a greater volume of interstitial fluid within their residual limbs than subjects who are more active (high K level ($K_3$, $K_4$)). The basis for this expectation is that active subjects adapt to become physiologically efficient, and as a result, they are in better health. Their reduced interstitial fluid reservoir size provides less resistance to interstitial fluid flow and thus more efficient transport. Less effort is needed in terms of arterial drive to transport fluid into the interstitial space. Further, with less stagnant fluid in the interstitial space, there is less chance of cell waste product buildup and thus, less potential for tissue breakdown. Therefore, active subjects would be expected to have a reduced limb volume change during the standing segments of data collection, compared to less active subjects. FIG. 3A is a schematic view 120 that illustrates a typical limb volume change occurring during a standing interval, as the applied socket pressure causes the interstitial pressure to increase and thus, interstitial fluid 124 to be expelled from a residual limb 122, so that the volume of the limb decreases with less interstitial fluid 126.

Another area of interest in regard to the present novel approach is investigating differences in the degree of residual limb volume change from one day to the next. Patients with substantial diurnal volume change variability must change their prosthesis accommodations accordingly. On one day, a patient might need to add three sock plies midday, while on another day, no added sock ply is needed. Particularly for low cognition patients or those with poor sensation in the residual limb, this need for inconsistent accommodation is difficult to manage. Residual limb soft tissues are put at risk if improper accommodation is performed. Clinical experience suggests that volume change variability is particularly prevalent in certain diabetic patients (due to inadequate glucose control, or medication non-compliance) and in patients with kidney dysfunction (hemodialysis). These patient groups are likely to undergo greater variability than others. The present novel approach addresses this problem by enabling evaluations that provide better understanding of the degree of day-to-day volumetric residual limb change, provide insight into its sources, and facilitate efforts to develop the bioimpedance tool into a device that can identify and characterize those sources. Thus, the bioimpedance volume measurements should enhance an understanding of these problems that will facilitate the design of more effective treatments.

Vacuum Assist

Clinicians and patients attempt to manage residual limb volume fluctuation through a variety of methods. The most common is to add stump socks to accommodate residual limb shrinkage. Also available are air-filled inserts (e.g., Pneu-Fit™, Prosthetic Concepts, Little Rock, Ark.; and, Pump-It-Up!™, Love Associates Inc, Batavia, N.Y.) and fluid-filled inserts (e.g., Active Contact System™, Simbex, Lebanon, N.H.; and, Volume Management Pads™, Ohio Willow Wood, Mount Sterling, Ohio) that are positioned between the limb and socket. Another technology is liners and sockets with electro-active or piezoelectric materials (or other "smart material") within them that change shape upon an applied electrical current or mechanical force. All of these products follow a similar strategy; they replace fluid displaced from the residual limb by adding volume within the socket. The limitation of these products is that they do not eliminate the root cause of the problem—limb volume reduction. Because of this limitation, there are detrimental ramifications. It is hard for a patient to know when to add socks, particularly if sensation is compromised, or if the patient's mental capacity is diminished. It can be difficult for some patients to remember to check the status of their socket fit. In sum, the burden is on the patient, and it can be a challenge for the practitioner to prescribe an effective treatment.

A recent novel approach to treating limb shrinkage problems is to keep the residual limb from shrinking rather than compensating for the shrinkage. VADs were introduced approximately 10 years ago by Carl Casper (TEC Interface Systems, St. Cloud, Minn.). There are now several products available (including Harmony System™ and E-Pulse System™, Otto Bock, Minneapolis, Minn.; LimbLogic™, Ohio Willow Wood, Mt. Sterling, Ohio; and, eVAC™, Smith Global, Laurie, Mo.). Evidence of enhanced interest in vacuum assist has appeared recently in the form of requests for Small Business Innovation Research (SBIR) proposals from funding agencies to further the technology and new corporate patents submitted since Casper's initial patent. At a recent meeting of the American Academy of Orthotists and Prosthetists, entire technical and educational sessions were devoted to vacuum assist technology. Further, vacuum assist costs are covered by insurance reimbursement, while other volume control technologies (e.g., air-filled bladders and fluid-filled inserts) are not. Thus, vacuum assist is increasing in prominence in the prosthetics field.

VADs work on the concept that applying a vacuum in the space between the limb and socket wall pulls residual limb soft tissues outward, retarding limb shrinkage and drawing fluid into the limb, particularly during the swing phase of ambulation. During the swing phase, vacuum assist keeps the interstitial fluid pressure low, thus enhancing fluid transport into the residual limb. In concept, with a proper setting of vacuum pressure, a balance can be achieved between the "outward" force generated during weight-bearing, which tends to drive fluid out of the interstitial space and into the venous vasculature, and the "inward" driving force facilitated by the vacuum, which draws fluid into the interstitial space from the arterial system.

Although proponents of vacuum assist have reported clinical success, others claim that vacuum assist is risky. (At least one adverse event report has been filed.) Some claim that vacuum assist does not control volume change at all—it simply creates such a tight suspension that the prosthesis feels tighter on the limb and thus, creates the sensation that no limb volume change has occurred. Some argue that the tight suspension puts fragile soft tissues at risk. Experiments conducted comparing limb volume changes using vacuum assist with not using vacuum assist are hardly convincing. Residual limb volume was measured on 10 amputee subjects by casting them after ambulation. Alginate casts were made immediately after the subject exercised for 30 min., by doffing the prosthesis and placing the residual limb in an alginate-filled tank. A fluid displacement modality was used to measure cast volume. No time interval between doffing and casting was specified, which is a substantial source of error in this experiment, since this time interval must be very carefully controlled. Limb enlargement after doffing, particularly after activity, has been shown to be highly sensitive to time. Even 30 s interval differences can change the volume measurement by as much as 5%. Given that vacuum assist showed only a 3.7% increase in limb volume from the beginning to end of the session, the reliability and quality of the measurement is in question. Furthermore (and without any negative implied comment), these studies were funded and co-authored by the company marketing the product (TEC Interface Systems, Waite Park, Minn.).

Practitioners are left with fundamental questions. Does vacuum assist really reduce diurnal shrinkage and stabilize limb volume? If so, how does it work, and how sensitive is limb fluid transport to the vacuum pressure setting set by the user? Further, for patients with much variability in day-to-day changes in limb volume, does converting to vacuum-assist reduce this variability? This last question is particularly relevant for some diabetic and most hemodialysis patients, since clinically, they often experience high day-to-day limb volume changes.

Bioimpedance is an ideal modality for assessing vacuum assist devices (VADs) and other volume management systems. Measurements are conducted while the residual limb remains within the socket, not after the prosthesis is doffed. This capability overcomes a major limitation in residual limb volume change assessment carried out by previous investigators. Further, measurement can be conducted during activity by the subject. Not only it is thus possible to accurately assess if and how much change occurs using vacuum assist, the analysis can be expanded to investigate when and during what activities volumetric changes take place. Is limb shrinkage during standing reversed during subsequent walking? Is it true that VADs improve limb fluid volume consistency? Because total contact sockets are used and vacuum pressure is the same from day to day, the socket is expected to restrict limb tissues to one size. If this is the case, then day-to-day volume changes should reduce when patients with inconsistent limb volume changes switch to VADs.

It is hypothesized that for subjects with large $\Delta V_{stand}$ values, during bioimpedance testing before VAD use (which is expected to reflect large interstitial fluid compartments in their residual limbs), VAD use should decrease those volume changes. These subjects are expected to undergo excessive shrinkage after starting on VADs. Their shrinkage is expected to be so excessive that it may be necessary to make a new socket for them. It is only subjects with large $\Delta V_{stand}$ values that are expected to experience this drastic limb reduction because they are the ones with such large interstitial fluid reservoirs at the outset. The evaluations will be conducted using the present novel approach.

A confusing feature of current electronic VADs is the vacuum pressure setting. The setting can be adjusted by a patient setting that can provide up to a maximum vacuum level of approximately 18-20 mm Hg pressure (i.e., to provide a partial vacuum at that pressure in the socket). Currently, according to product manuals, the vacuum level should be set based upon what is comfortable to the patient for the activity at hand. Some practitioners believe that a high level of vacuum (i.e., a very low socket pressure) is detrimental to residual limb tissues. It is expected that an excessive setting, i.e., beyond that needed to achieve good suspension, will increase the fluid transport in the limb. In other words, subjects will lose more volume during standing (when the VAD is expected to do little towards increasing limb volume) and then gain more during walking, compared with that achieved at a lower vacuum pressure setting. This increased transport is expected to be detrimental to subjects with at-risk transport physiology, i.e., subjects with fragile limb fluid systems. It may put them at higher risk of injury. Insight to resolving these questions can be provided through bioimpedance analysis.

Comments from the prosthetics community indicate that much adjustment is required on the part of the patient to use a VAD device regularly, for example, turning it off while sitting and adjusting the pressure magnitude for different activities. Bioimpedance measurements should help to establish when vacuum pressure adjustment is needed and provide a starting point for an automated system to perform these adjustments without intervention from the user. Further details for a system that uses bioimpedance as a feedback mechanism to automatically adjust the level of vacuum applied by a VAD device are discussed below.

Bioimpedance Studies

It is important to recognize that in the data presented here, the percentage volume changes are defined as being relative to the conductive tissues within the residual limb. This characterization does not include bone or adipose tissue. This practice is the convention in the bioimpedance field.

Results from the 15 subjects were analyzed using t-tests to investigate differences between means, between the add-sock and no-add-sock groups, and between the $K_1/K_2$ activity level (low activity) and $K_3/K_4$ activity level (high activity) groups (SPSS). Boxplots of the data are shown below for sock addition (FIG. 5A) and activity level (FIG. 5B).

Subjects with diurnal volume change complications requiring intervention (sock addition) showed deviations from the results illustrated in FIG. 4 as discussed below. Results from the sample of 15 subjects showed the following:

Subjects reduced in volume over the 5 min. interval of standing with equal weight bearing, as expected. Standing caused the interstitial fluid pressure to rise, pushing fluid out of the interstitial space into the venous compartment (FIG. 3A). The change in volume during standing, $\Delta V_{stand}$, was significantly smaller (p=0.005) for the subject group that did not add socks during the day, compared with the subject group that did add socks, as shown in a graph 150 of FIG. 5A, specifically in the first panel on the left. Thus, this result is consistent with an expectation that subjects with large diurnal volume changes have large interstitial fluid reservoirs and/or relatively inefficient interstitial to venous transport systems.

Over the course of the 5-minute walking interval, all subjects underwent residual limb enlargement except subjects S#2, S#8, and S#10 who underwent shrinkage. Their volume shrinkages were 0.2% (S#2), 0.9% (S#8), and 0.8% (S#10). All of these subjects displayed a gradual shrinkage over the course of the session. This gradual shrinkage did not occur for the other subjects. Interestingly, these three individuals were the only subjects with known vascular insufficiency or vasodilation issues. S#2 had congestive heart failure; S#8 had vascular disease; and S#10 consumed alcohol (a vasodilator in the short term) immediately before the session. Thus, there was a link between one of the analysis features ($\Delta V_{walk}$) and this aspect of subject health. One of these cases (S#8) is discussed in more detail below (Case 1). Statistical analysis of the entire sample showed that the change in $\Delta V_{walk}$ was significantly smaller (p=0.011) for the subject group that did not add socks during the day, compared with the subject group that did add socks, as shown in FIG. 5A, second panel from the left.

$V_{ECF}$ decreased for most of the subjects between the end of the first walking interval and the end of the second walking interval ($\Delta V_{wk1\_wk2}$). Two of the three subjects that did not, S#7 and S#15, had high blood pressure without heart disease, and these were the only subjects with this condition documented in their patient histories. The third subject S#9 did not have an edema-inducing disease. However, she was a recent amputee who experienced severe trauma to her limbs and thorax, and these factors may have been influential here. Statistical analysis of the entire sample showed that the subject group that did not add socks during the day had smaller $\Delta V_{wk1\_wk2}$ values compared with the subject group that did add socks, but the difference was not statistically significant (p=0.170) (see FIG. 5A, third panel from the left).

Consideration of the sum of the all three features ($\Delta V_{sum} = \Delta V_{stand} + \Delta V{walk} + \Delta V_{wk1\_wk2}$) showed a clear delineation between sock-adders and non-sock-adders as shown in FIG. 5A, fourth panel from the left. $\Delta V_{sum}$ was significantly greater for sock adders than for non-sock adders (p=0.000). It is important to note that the bioimpedance measurement (morning measurement) was conducted before a sock was added during the day. Thus, increased mechanical loading from the sock being added to the prosthesis could not have induced a change in the measurement, because the sock had not yet been added.

Further analysis to investigate a link between subject characteristics and the volume change variables revealed no significant difference (p>0.05) between the analysis features $\Delta V_{stand}$, $\Delta V_{walk}$, and $\Delta V_{wk1\_wk2}$ and any of the following: gender, age, locking pin presence, usual AM sock thickness, years since amputation, and residual limb length. The small sample size must be considered when interpreting this result. However, $\Delta V_{stand}$ was significantly higher (p=0.035) for the $K_1/K_2$ activity group than for the $K_3/K_4$ activity group; $\Delta V_{walk}$ and $\Delta V_{wk1\_wk2}$ were not significantly different (p=0.14 and 0.64, respectively) for $K_1/K_2$ vs. $K_3/K_4$ ambulators, as is evident in a graph 152 in FIG. 5B. It is interesting that only $\Delta V_{stand}$ correlated well with activity, adding support to the hypothesis that less active subjects have greater interstitial fluid reservoirs in their residual limbs than more active subjects.

Also considered were the data collected during pre-donning and post-doffing to see if there was any relationship with sock addition. Results showed that the pre-donning minus post-doffing volume difference was not significantly different between sock-adders and no-sock adders (p=0.45). Residual limb swelling measured over the first two minutes after doffing also was not significantly different for the two groups (p=0.41). This result adds support to the conclusion that pre- and post-doffing data are not useful in assessing the volume changes. It is now clear that in-socket assessment is needed.

The volume change as a percentage of total limb volume during the first 10 min. after doffing for the 15 subjects studied here, 0.5% to 8.0%, was comparable to that reported in the literature using a non-contact optical imaging modality. A direct comparison of the two techniques is not possible because: (1) the electrodes interfere with the optical imaging system making simultaneous measurement not meaningful, and (2) the bioimpedance instrument measures from a different region than the optical device (i.e., between the electrodes). In-socket limb volume comparisons cannot be conducted because the optical imaging measurement system cannot image through the socket wall. Thus, the bioimpedance measurement magnitudes are on the order of those reported in the literature for the only data available to which they can be compared, i.e., post-doffing data. These results help support validity of bioimpedance measurement for evaluating changes in residual limb volume.

In analyzing the results of this study, only features of the data for which the residual limb position in the socket did not drastically change were investigated. Volume with the prosthesis donned was not compared against volume with the prosthesis doffed, for example. There was concern that substantial position differences of the limb in the socket would appreciably affect the limb shape. In other words, a volume difference might be measured that was due to the fact that an appreciable force was applied by the socket at the posterior proximal aspect during sitting, distorting the shape of the socket. Thus, while volume changes due to this source are real and are being correctly measured by the bioimpedance instrument, they are not of primary clinical interest here. A decision was made to analyze only conditions for which the limb position in the socket did not drastically change, i.e., the analysis features described above. In addition to the statistical analyses described above, an individual case study of the data proved interesting and useful. Four case studies illustrating how the data facilitated interpretation and treatment are described below.

Case 1 (S#8): This case studied a 69 year old male who had been an amputee for 23 years. He was 105.0 kg in mass and 185 cm in height and had his lower leg amputated due to vascular disease and gangrene. For the past 2½ years, he was diabetic. A K-2 level ambulator, this individual used a trans-tibial socket with an expanded polyethylene foam liner and neoprene suspension sleeve. He was retired and used a bicycle for transportation instead of walking.

Results from this subject were much different than those of the healthy subject that are shown in FIG. 4. There was a gradual ECF volume decrease over the session. Most notably, the subject's limb did not enlarge when the walking intervals were initiated; instead, it continued to decrease in volume. This result is consistent with the subject's health status. His vascular insufficiency resulted in a reduced arterial to interstitial fluid drive during walking compared with healthy subjects in the sample. Without sufficient vascularity, fluid transport into the residual limb did not increase upon the initiation of walking. Of particular note in this case was the subject's interpretation of his fitting. He was adamant that over the course of the session, his residual limb was increasing in volume, not decreasing. He was sure that he was experiencing distal discomfort because his residual limb was swelling so excessively in the socket. He felt that the induced tightness was causing a slight throbbing sensation.

After two sessions with similar data collected on the subject, the research practitioner showed this subject the bioimpedance data. The subject was surprised that his limb was actually decreasing in ECF volume over the session. Interestingly, he quickly accepted the data as valid. In the subsequent session one month later, he was using a smaller socket, and his limb was much healthier. The improvement in his limb tissue health was marked. In the research practitioner's view, this attitude change to accept the new socket was due to his being shown the bioimpedance ECF volume change data. For months, he had refused to use the new prosthesis with the smaller socket. Showing and interpreting for him the bioimpedance data helped to convince him that using the new socket was in his best interest.

Case 2 (S#9): This subject was a 25 year old female who had her amputation six months earlier, due to a traumatic injury. She was in good health, a K-4 level ambulator, and an avid long-distance runner. She was 58.2 kg in mass and 160 cm in height. She used a trans-tibial socket with a silicone liner and locking pin. Testing results on this subject showed substantial ECF volume decreases during standing (1.4%) and moderate increases during walking (0.5%), as shown in a graph 160 in FIG. 6A. She was very early post amputation, approximately six months since surgery. At 12 months post amputation; however, her ECF volume decrease during standing was less (0.9%), and the increase in ECF volume during walking was less (0.2%), as shown in a graph 162 in FIG. 6B. Clinically, she had transitioned from adding two sock ply midday, to not adding any ply during the day. Instead, the additional two ply were added on in the morning when she initially donned her prosthesis.

Case 3 (S#2): This subject was a 64 year old male unilateral amputee who had his amputation 42 years prior. His cause of amputation was trauma. He was 90.5 kg in mass and 183 cm in height and was a K-3 level ambulator. Although he was retired, he reported walking frequently. He used a trans-tibial socket with a wool sock, an expanded polyethylene foam liner, and neoprene suspension. He had congestive heart failure and was taking medication for it. Results from sessions for this subject over many months showed very stable and consistent ECF volume changes.

Results from a typical session shown in a graph 170 in FIG. 7A demonstrate a 1.3% ECF volume decrease during standing and a 0.2% decrease during walking. Results were essentially identical over a 16 month period.

Drastically different results were obtained in a subsequent session. Instead of showing stable curves, his residual limb ECF volume decreased during the session, particularly during the walking interval (2.0% and 3.5% ECF volume decreased during standing and walking intervals, respectively), as shown in a graph 172 in FIG. 7B, similar to results for Case 1 above. Upon querying by the study practitioner about recent changes to his diet or daily routine, the subject admitted that he had eaten a lot of ham and other salty foods over the past three weeks, unlike his usual low-salt diet. It is likely that the high salt intake coupled with his congestive heart failure condition caused him to retain much interstitial fluid, providing greater resistance to fluid transport from the arterial compartment to the interstitial space. This reduced fluid transport would explain the decrease in residual limb volume during walking.

Case 4 (S#1): This male was 60 years of age and had his amputation 4 years ago, due to traumatic injury. He was 73 kg in mass and 175 cm in height and had no abnormalities other than his unilateral amputation. He used a trans-tibial socket with an elastomeric liner with a locking pin. A K-4 level ambulator, this subject regularly walked and played golf and racquet sports. He did not add socks or perform any prosthesis modification over the course of the day to accommodate limb volume reduction except under extreme physical exertion. In that condition, he would add one sock. Data from this subject were collected in both a morning session and an afternoon session five hours later. As expected, his limb volume reduced from the AM to PM. The volume change was 1.5 ml. This change was not sufficient to require sock addition, consistent with clinical expectation that a 1.5 ml volume change was not clinically significant. Further, his low $\Delta V_{sum}$ (1.3%) matched his low diurnal volume change and no need for sock addition. It is relevant that the bioimpedance instrument can pick up this small volume reduction, and that the within-session data are indicative of the AM to PM volume change.

A second preliminary study was conducted to investigate bioimpedance changes with the use of VADs. A total of four subjects participated in this investigation. Because so few subjects were tested, these findings are discussed as a series of case studies.

Case A: The subject was a 42 year old male unilateral amputee, 122.7 kg in mass and 180.3 cm in height, who had his amputation four years earlier as a result of a traumatic injury. He was in good health, with no abnormalities other than his limb amputation. For the past 11 months, he had been using a VAD (SmithGlobal™) and was very satisfied with it. This subject was the only one tested who regularly used a vacuum assist unit.

Unlike other subjects described above, this subject demonstrated a relatively continuous high rate of limb volume increase during the walking intervals, as shown in a graph 180 in FIG. 8. The average rate of change during the two intervals was 0.34%/min. One possible interpretation is that the vacuum facilitated this volume increase during walking. Studies attempted with the vacuum turned off were not successful, because the subject could not walk comfortably with the prosthesis.

Unlike the subject of Case A, the other three subjects did not regularly use VADs for extended periods. Nor did their practitioners recommend vacuum assist. They were participating in research studies that required use of a vacuum assist prosthesis for a three week period. All had been wearing the vacuum assist unit for three weeks when bioimpedance data were collected.

Case B: This was Subject #1 described above. He wore a Hannony™ VAD system (Otto Bock), which is a manual, not electronic, vacuum assist unit. A pumping bladder in the distal end of the socket creates a vacuum pressure when the patient walks. Vacuum is generated only during walking.

Case C: This subject was a 47 year old male unilateral amputee, 77.3 kg in mass and 188.0 cm in height, who had his amputation 23 years earlier as a result of a traumatic injury. He was in good health with no abnormalities other than his limb amputation. This subject also wore a Harmony™ VAD system.

Case D: This was a 33 year old male unilateral amputee subject, 102.3 kg in mass and 188.0 cm in height, who had his amputation 2 years prior as a result of a traumatic injury. He was in good health with no abnormalities other than his limb amputation. This subject wore an ePulse™ system (Otto Bock), which is an electronic vacuum assist unit. The unit has four vacuum settings (1, 2, 3, 4) with the maximum (the 4 setting) corresponding to a pressure of approximately 20 mm Hg.

All three of these subjects showed greater peak-to-peak volume changes during walking with the vacuum on than with the vacuum off, as shown in a graph 190 in FIG. 9. This result is consistent with an expectation that vacuum assist enhances suspension. Better suspension and less pistoning would be expected to reduce the volume fluctuation that occurs between the stand and swing phases of gait. It is worth noting that the sampling rate of the bioimpedance instrument is 1 Hz. This frequency is less than the walking frequency, and is thus below the Nyquist rate. However, analysis of the high to low range over the course of the 5-minute walking interval is acceptable because step-to-step changes are being assessed, and there are many cycles over the 5-minute interval.

The Case D subject participated in an additional session where the vacuum setting on the electronic vacuum unit was adjusted after each 2-minute walking interval. Results showed that during the portion when the vacuum pressure was successively increased, residual limb volume increased with each increase in vacuum setting, 1 to 2 to 3 to 4, as shown in a graph 200 in FIG. 10. After a 2-minute sitting interval, the subject walked for additional walking intervals, this time with the vacuum decreased from setting 4 to 3 to 2 to 1. The residual limb volume vs. time data remained approximately consistent for the 4, 3, and 2 settings. However, for the last interval (setting 1), the residual limb volume decreased (see FIG. 10). Because the pump was heard during trials with VAD control at the 3 and 2 settings, it was expected that the setting 4 vacuum level was not maintained during the setting 3 interval, nor was the setting 3 vacuum level maintained during the setting 2 interval. It appeared that the results are reflecting the viscoelastic nature of residual limb tissues—soft tissue takes longer to reduce in volume after a vacuum setting decrease than to increase in volume after a vacuum setting increase. Because patient disease might involve arterial complications, venous complications, or both, bioimpedance data should not be correlated with disease (e.g., cardiac insufficiency). Instead the data should be correlated with the patient's arterial functional status and venous functional status.

Exemplary System for Automatic Bioimpedance Feedback Control of VAD Settings

FIG. 11 illustrates a functional block diagram of an exemplary embodiment for a system 220 that uses bioimpedance measurement of the volumetric changes in a residual limb 224 to control a volume management device disposed on the prosthesis. The device could be, for example, a vacuum assist device intended to control residual limb volume, or a fluid-filled insert, or a shape-controlled liner intended to control socket volume (i.e., volume within the socket available to the residual limb). A bioimpedance monitor and volume management controller 240 disposed, for example, on a prosthesis shank 238, detects the voltage across pairs of voltage electrodes, such as electrodes 230 and 232, in response to a current injected into the limb at spaced apart current electrodes 226 and 228. The current and voltage signals are conveyed between the current/voltage electrodes and bioimpedance monitor. Based on volume changes determined in 240, adjustments are made (e.g., the level of vacuum, or the amount of fluid, or the shape of socket (i.e., a variable liner), and/or internal components) to a dynamic volume control device 244 and a socket interface 248. The socket interface can be a fluid line if fluid volume or pressure is used to compensate for changes in residual limb volume, or can be either a wired or a wireless signal if the signal controls the management of volume of the residual limb or the volume in the socket. A battery power supply 242 provides the electrical energy used to energize the bioimpedance monitor and dynamic volume controller 244. In response to the changes in ECF and or ICF volume in limb 224 by the bioimpedance measurements, the bioimpedance monitor and dynamic volume controller provide a control signal through a line 246 that automatically adjusts the volume control device to one or more compartments of prosthetic socket 222 via controller interface 248. For example, for a vacuum assist device, the control signal would set the level of vacuum applied to prosthetic socket 222 through socket interface 248. For fluid-filled or air-filled inserts, the control signal would adjust the amount of fluid in the inserts. For liners with shape-controlled or smart materials, the control signal would adjust voltage to the electro-active materials thus control deformation of the material.

Thus, an appropriate fit between the prosthetic socket and the residual limb of the subject is automatically maintained by system 220 during periods in which the subject engages in different types of activity, by detecting changes in volume of the residual limb and providing an appropriate level of dynamic volume control of the residual limb and/or prosthetic socket and it internal components. A similar system can be used for subjects with prosthetic sockets on both legs by modifying the embodiment shown in FIG. 2C to provide sensing and feedback signals to control a second dynamic volume control device in each of the sockets, so as to provide the appropriate dynamic volume changes to each socket.

The signal from the bioimpedance monitor and controller can also be used to control a device on the prosthesis, such as a micro-controlled foot/ankle, which modifies prosthetic fit, gait, and/or performance. The feedback signal can automatically compensate the action of the foot/ankle for the change in volume of the residual limb as the subject engages in different activities. For example by modifying the suspension of the prosthesis, the force applied to the residual limb during activity can be varied, which will then affect the amount of fluid in the limb in response to the feedback signal.

FIG. 12 illustrates a functional block diagram of an exemplary alternative embodiment 300 that includes wireless power transmission and wireless data transmission for a plurality of voltage sensing electrodes, such as voltage electrodes 306 and 308, so as to eliminate cables and cable connectors coupled to them. Wireless power transmission can also optionally be employed for energizing current injecting electrodes 302 and 304. In this exemplary embodiment, eight voltage electrodes are embedded within an "electrode patch" 310 that is affixed to the skin of a residual limb 312. The patch backing is a flexible, breathable non-conductive biocompatible material that is comfortably tolerated by the skin for days or weeks. Flexible circuit board electronics are contained within the electrode patch. An operational amplifier 314 (only one labeled) is positioned adjacent to each voltage electrode to enhance the robustness of the signal provided thereby near the sensing location. The operational amplifier converts the high impedance sensed voltage from the electrodes to a low impedance voltage. Because the electrodes are very small and the impedance of the measurement system is high, amplification immediately adjacent to the electrodes provides a better output signal. A power receiver 316 and a data transmitter 318 (both of which are coupled to the amplifiers via a flexible circuit) are also disposed within the patch. They communicate wirelessly with a nearby radio frequency (RF) inductive power source 320 and with a data receiver 322 that are both positioned on or in the prosthesis, such as in the inner socket wall so as to be immediately adjacent to the patch and potentially separated from the electrodes by a liner/sock, or other intermediate material. The RF inductive power source wirelessly conveys power to the electronic components, such as amplifiers 306, which are disposed on the patch. The current injecting electrodes may or may not be part of the patch containing the voltage electrodes.

In the exemplary embodiment shown in FIG. 12, current injecting electrodes 302 and 304 are disposed within a liner that envelops the residual limb, including part of the limb proximal to the socket with contact connections between the liner and socket that connect upon the user donning the socket so as to provide a direct connection to embedded bioimpedance electronics 330, which can be mounted on the shank of the prosthesis or at some other convenient location that moves with the user. Included with embedded bioimpedance electronics 330 are a WiFi, WiMax, Bluetooth, or other wireless link 332 to a PC (not shown in this Figure). A dynamic volume control device 334 that responds to the signal indicative of changes in the volume of the residual limb determined by the bioimpedance measurement can be provided to transmit a volume control signal (conveyed either by wire or wirelessly) that is used to control a volume control device 338. The volume control device modifies either the volume of the residual limb, or the volume in the socket, as discussed above. The volume control signal can also be used to control a device on the prosthesis, such as a micro-controlled foot/ankle, which modifies the prosthetic fit, gait, and/or performance, to affect the force experienced by the residual limb and thereby change the volume of the limb by modifying the amount of ECF in the residual limb. A rechargeable battery power supply 336 is used to provide power to RF inductive power source that provides power to the components on patch 310 and to provide power to embedded bioimpedance electronics 330 and other electrically energized components.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using bioimpedance to measure volumetric changes of a residual limb of a person with a limb amputation over time, while the person is wearing a prosthetic socket on the residual limb, comprising the steps of:
    (a) injecting an alternating current into tissue of the residual limb, between two longitudinally spaced-apart points along the residual limb;
    (b) detecting a change in voltage at a plurality of points that are intermediate the two spaced-apart points; and
    (c) based upon the change in the voltage, using a model for determining a change in the volume of the residual limb over time.

2. The method of claim 1, further comprising the step of controlling a frequency of the alternating current to be within a frequency range from about 1 kHz to about 1 MHz.

3. The method of claim 1, further comprising the step of determining changes in the volume of the residual limb during periods of different types of activity.

4. The method of claim 1, further comprising the step of using the change in volume of the limb to determine if the prosthetic socket should be changed to provide a new prosthetic socket that better fits the residual limb of the person.

5. The method of claim 1, further comprising the steps of using the change in volume of the residual limb to determine a non-essential fluid volume and an essential fluid volume to aid in designing a new prosthetic socket for the residual limb.

6. The method of claim 1, further comprising the step of using the change in volume of the residual limb to determine a cause of a volume control problem of the person.

7. The method of claim 1, further comprising the step of using a signal indicative of the change in volume of the residual limb as a feedback signal to control a device that modifies the volume of the residual limb, to automatically compensate for the change in the volume of the residual limb as the person engages in different activities.

8. The method of claim 1, further comprising the step of using a signal indicative of the change in volume of the residual limb as a feedback signal to control a device that modifies a volume of at least one of the prosthetic socket, and a component disposed in the prosthetic socket that can change an available volume in the prosthetic socket, so as to automatically compensate for the change in the volume of the residual limb as the person engages in different activities.

9. The method of claim 1, further comprising the step of using a signal indicative of the change in volume of the residual limb as a feedback signal to control a device in at least one of a prosthetic foot, a pylon, and an alignment adaptor, to modify a force applied to the residual limb through the prosthetic socket, so as to automatically compensate for the change in the volume of the residual limb as the person engages in different activities.

10. The method of claim 9, further comprising the step of wirelessly transmitting the feedback signal that controls the device to the device.

11. The method of claim 1, further comprising the step of using the change in volume of the residual limb to assist in determining an appropriate treatment of the person, and reduce volume fluctuations of the residual limb.

12. The method of claim 1, further comprising the step of wirelessly transmitting the voltage detected at the plurality of points to a receiver that is mounted proximate to the prosthetic socket, for processing to determine the change in volume of the residual limb.

13. The method of claim 1, further comprising the steps of
    (a) amplifying the voltages detected at the plurality of spaced-apart points with electronic amplifiers that are included with voltage electrodes on a patch applied to the residual limb, to produce voltage signals; and
    (b) wirelessly energizing the electronic amplifiers with an inductive power signal that is transmitted from an inductive power source disposed on the prosthetic socket, proximate to the patch.

14. A method for assessing volumetric changes of a residual limb of a person with a limb amputation, comprising the steps of:
    (a) coupling a first current electrode to tissue at a first position on the residual limb, and a second current electrode to tissue at a second position on the residual limb that is more distal than the first position;
    (b) coupling a plurality of voltage electrodes to tissue on the residual limb, at spaced-apart positions that are disposed intermediate the first position and the second position;
    (c) applying an alternating current to the first and second current electrodes;
    (d) sensing a voltage between pairs of the plurality of voltage electrodes;
    (e) based on the voltage between the pairs of the plurality of voltage electrodes, determining a change in a volume of the residual limb over time; and
    (f) providing a signal indicating the change in the volume of the residual limb over time.

15. The method of claim 14, wherein the step of determining the change in the volume of the residual limb comprises the step of employing modeling of bioimpedance characteristics of the residual limb to determine the change in volume of the residual limb.

16. The method of claim 15, wherein the step of employing modeling comprises the step of employing Cole modeling to determine the change in volume, wherein the Cole modeling uses an equivalent circuit corresponding to an extracellular resistance, an intracellular resistance, and a cell membrane capacitance.

17. The method of claim 16, wherein the voltage sensed between a pair of the voltage electrodes is indicative of a volume change of a generally cylindrical segment of the residual limb disposed between the voltage electrodes of the pair.

18. The method of claim 17, wherein the step of employing Cole modeling comprises the steps of applying a nonlinear weighted least-squares curve-fitting to a multi-frequency impedance spectrum of the voltage sensed between pairs of the voltage electrodes; and, extrapolating bioimpedance data at different frequencies of the alternating current applied to the first and second current electrodes.

19. The method of claim 18, further comprising the step of converting the bioimpedance data to volume data through modeling, based on the principle of volume conduction.

20. The method of claim 14, wherein the step of applying the alternating current comprises the step of applying the alternating current at a plurality of different frequencies selected from a range of about 1 kHz to about 1 MHz.

21. The method of claim 20, wherein the step of applying the alternating current at the plurality of different frequencies includes the steps of determining an extracellular bioimpedance using a lower frequency in the range, and determining both the extracellular bioimpedance and an intracellular bioimpedance using a higher frequency in the range.

22. The method of claim 14, further comprising the step of using the signal indicative of the change in volume of the limb as feedback, to control a device that modifies the volume of the residual limb, so that the volume of the residual limb is automatically controlled while the person engages in different activities.

23. The method of claim 14, further comprising the step of using the signal indicative of the change in volume of the residual limb as feedback, to control a device that modifies a volume of at least one of a prosthetic socket worn on the residual limb, and a component disposed in the prosthetic socket that can change an available volume in the prosthetic socket, so as to automatically compensate for the change in the volume of the residual limb as the person engages in different activities.

24. The method of claim 14, further comprising the step of using the signal indicative of the change in volume of the residual limb as feedback, to control a device in at least one of a prosthetic foot, a pylon, and an alignment adaptor, to modify a force applied to the residual limb through a prosthetic socket worn on the residual limb, so as to automatically compensate for the change in the volume of the residual limb as the person engages in different activities.

25. The method of claim 22, further comprising the step of using the signal indicative of the change in volume for controlling a vacuum assist device to vary a level of a vacuum applied to a prosthetic socket that is fitted to the residual limb, wherein the vacuum controls an amount of an extracellular fluid buildup within the residual limb to control the volume of the residual limb and maintain a comfortable fit of the residual limb within the prosthetic socket.

26. The method of claim 14, further comprising the step of using the signal indicative of the change in volume to graphically indicate the change in the volume of the residual limb over time.

27. The method of claim 14, further comprising the step of transmitting the signal indicative of the change in volume to a computing device for further processing.

28. The method of claim 27, further comprising the steps of storing data comprising the signal indicative of the volume change, for an extended period of time; and, communicating the data to the computing device from the storage device, when desired.

29. The method of claim 14, further comprising the step of determining the change in volume while the person is engaged in different types of activities, to assess the extent of the volume change in each type of activity.

30. A system for assessing volumetric changes of a limb of a person with a limb amputation, while the person is wearing a prosthetic socket, comprising:
(a) a first current electrode and a second current electrode that are configured to couple electrically to tissue respectively at a proximal position and a distal position along a longitudinal axis of a limb;
(b) a plurality of voltage electrodes that are configured to couple to tissue of the residual limb at spaced-apart positions intermediate the first and the second current electrodes;
(c) an alternating current source coupled to the first and the second current electrodes, the alternating current source producing an alternating current for injection into tissue of a limb; and
(d) a processing device that is coupled to the voltage electrodes, the processing device processing a voltage sensed across pairs of the plurality of voltage electrodes, to produce a signal indicative of a change in the volume of the residual limb over time.

31. The system of claim 30, wherein the processing device processes the voltage sensed across the pairs of the plurality of voltage electrodes using modeling related to a bioimpedance of tissue.

32. The system of claim 31, where the voltage sensed between a pair of the voltage electrodes is indicative of a volume change of a generally cylindrical segment of the residual limb disposed between the voltage electrodes of the pair.

33. The system of claim 32, wherein the alternating current source produces alternating current at plurality of different frequencies, and where the processing device applies a non-linear weighted least-squares curve-fitting to a multi-frequency impedance spectrum of the voltage sensed between adjacent pairs of the voltage electrodes and extrapolates bioimpedance data at a plurality of different frequencies of the alternating current applied to the first and second current electrodes.

34. The system of claim 33, wherein the plurality of different frequencies are in a range from about 1 kHz to about 1 MHz.

35. The system of claim 34, wherein the alternating current source applies current to the first and second current electrodes at a lower frequency in the range to enable the processing device to determine an extracellular bioimpedance and applies current to the first and second current electrodes at a higher frequency in the range to enable the processing device to determine both the extracellular bioimpedance and an intracellular bioimpedance.

36. The system of claim 30, wherein the processing device is configured to couple the signal indicative of the change in the volume to a volume control device that is used to vary a level of a vacuum applied to a prosthetic socket that is fitted to the residual limb, so that the level of the vacuum applied to the prosthetic socket is varied to control an amount of an extracellular fluid buildup within the residual limb, and thereby, to control the volume of the residual limb and maintain a comfortable, healthy, or stable fit of the residual limb within the prosthetic socket.

37. The system of claim 30, wherein the processing device is configured to couple the signal indicative of the change in the volume to a volume control device that is used to vary a volume of at least one of a prosthetic socket worn on the residual limb, and a component disposed in the prosthetic socket that can change an available volume in the prosthetic socket, so as to automatically compensate for the change in the volume of the residual limb as the person engages in different activities.

38. The system of claim 30, wherein the processing device is configured to couple the signal indicative of the change in the volume to a volume control device that is used to control at least one of a prosthetic foot, a pylon, and an alignment adaptor, to modify a force applied to the residual limb through a prosthetic socket worn on the residual limb, so as to automatically compensate for the change in the volume of the residual limb as the person engages in different activities.

39. The system of claim 30, wherein the processing device is coupled to storage media for storing data comprising the signal indicative of the change in the volume of the residual limb over time, so that the data can be downloaded over a link when desired.

40. The system of claim 30, wherein the processing device is coupled to a wireless transceiver for transmitting the signal indicative of the change in the volume to a receiving station.

* * * * *